United States Patent [19]

Birrenbach et al.

[11] Patent Number: 5,631,296
[45] Date of Patent: May 20, 1997

[54] DRUGS CONTAINING S(+)-IBUPROFEN

[75] Inventors: Gerd Birrenbach, Kappel; Rolf-Dieter Juch, Wangen, both of Switzerland

[73] Assignee: Spirig AG, Pharmazeutische Praeparate, Egerkingen, Switzerland

[21] Appl. No.: 307,486

[22] Filed: Sep. 16, 1994

Related U.S. Application Data

[63] Continuation of Ser. No. 69,152, May 28, 1993, abandoned.

[30] Foreign Application Priority Data

Dec. 1, 1992 [EP] European Pat. Off. .............. 92810938

[51] Int. Cl.$^6$ ...................................................... A61K 31/19
[52] U.S. Cl. ........................ 514/570; 514/557; 514/960; 514/962; 514/947
[58] Field of Search ................................ 514/570, 557, 514/960, 962, 947

[56] References Cited

U.S. PATENT DOCUMENTS 4,851,444  7/1989  Sunshine et al. ...................... 514/570

FOREIGN PATENT DOCUMENTS 0267321  5/1988  European Pat. Off. .
0288732  11/1988  European Pat. Off. .
0308665  3/1989  European Pat. Off. .

OTHER PUBLICATIONS

Wechter, W.J. et al Chirality, (1993) 5 (7) 492–4.

Romero A.J. et al, J Pharm. Belg (1993 Jan.–Feb.) 48 (1) 27–32.

*Primary Examiner*—Paul J. Killos
*Attorney, Agent, or Firm*—Lahive & Cockfield

[57] ABSTRACT

Rapid-release S(+)-ibuprofen pellets are proposed whose bioavailability is comparable to that of commercially available racemate formulations. The rapid release of the active substance is promoted by using small amounts of basic inorganic salts, preferably sodium carbonate, or dilute alkali metal hydroxide solutions. Pellets with an active substance content of 90–99% by weight are obtainable in this way. The pellets are suitable for the application of coatings. Pellets with a protective coating can be compressed directly to tablets in this form and with small amounts of suitable tableting adjuncts. The use of the pharmacologically active S(+)-ibuprofen and of the small amounts of adjuncts required makes it possible to prepare compact pharmaceutical forms.

47 Claims, 17 Drawing Sheets

DRUGS CONTAINING S(+)-IBUPROFEN

This application is a file wrapper continuation of application Ser. No. 08/069,152, filed on May 28, 1993, claiming priority to EPO application No. 92810938.8, filed on Dec. 1, 1992, now abandoned.

Ibuprofen, or 2-(4-isobutylphenyl)propionic acid, is known as a non-steroidal antiinflammatory (NSA) exhibiting a good antiinflammatory, analgesic and antipyretic action. It is used in particular in the therapy of chronic polyarthritis and of osteoarthritis. Ibuprofen also exhibits a good action in the treatment of dysmenorrhea, gout and mild to moderate pain. Ibuprofen was used in clinical practice for the first time in 1969 and extensive experience of its application has been gained.

As an arylpropionic acid derivative, ibuprofen contains an asymmetric carbon atom. In all commercially available preparations, ibuprofen is present as the racemate, i.e. as a 50:50 mixture of the two enantiomers, R(−)- and S(+)-ibuprofen. The pharmacological activity of ibuprofen, like that of most NSAs, is in the inhibition of prostaglandin synthesis by binding to the cyclooxygenase subunit of the enzyme prostaglandin synthease. This therapeutically relevant mechanism of action has been found in vitro only for the S(+) enantiomer, tiomer, although this enantioselectivity could not be confirmed in vivo. The explanation for this observation is that the R(−) enantiomer is converted in vivo to the pharmacodynamically active S(+) enantiomer. This conversion is an enzymatic process in which only the R(−) enantiomer participates, i.e. it proceeds stereoselectively and in one direction only. This has been proved in almost all species of laboratory animals and in humans.

It has become a widely held view in recent years that, where possible, chiral active substances should be separated into the corresponding enantiomers. The relative pharmacodynamic activities of the enantiomers and their possible pharmacokinetic and metabolic differences have been investigated. It has become recognized here that there is even the possibility of molecular interactions at the site of action and/or during transport through biological membranes. In the special case of ibuprofen, it could be assumed that the rapid conversion of the R(−) enantiomer to the active S(+) form justifies the use of the racemate. However, a detailed analysis of the relevant literature shows that there are marked advantages associated with using the S(+) enantiomer by itself. These recent results can be summarized as follows:

The conversion of R(−) to S(+) is incomplete and shows a considerable variability, so the effective dose of S(+)-ibuprofen which a patient's body absorbs can scarcely be determined accurately in advance. The binding to the serum proteins, which plays a major role in the case of the NSAs, is stereoselective, the R(−) and S(+) forms competing for the binding site. The proportion bound is therefore dependent on the relative amounts of the two enantiomers in the plasma. This has significant consequences on the diffusion of the active substance into therapeutically relevant compartments such as e.g. the synovial fluid. The multienzymatic reaction leading to the conversion of the R(−)-ibuprofen begins with the selective binding of this R(−) enantiomer to coenzyme A. This results in the formation of symmetrical thioesters, which are recognized by the organism as "fatty acid esters" and incorporated into the fatty tissue, from which they are very slowly eliminated. Accordingly, chronic administration of the racemate leads to an accumulation of the R(−) enantiomer in the fatty tissue. Although no toxic effects have so far been observed which are directly attributable to this accumulation, the prolonged presence of the active substance in the organism and the retarded elimination represent undesirable characteristics which could achieve toxicological significance, e.g. in the case of hypersensitivity. It therefore seems justified to replace the racemate with the active S(+) enantiomer.

It has been shown that, after oral administration, the rate of absorption from the gastrointestinal tract has a direct influence on the extent of the conversion. This contributes to the above-mentioned variability and also has direct consequences for the bioavailability and the bioequivalence of different pharmaceutical formulations of the racemate. This is especially true of pharmaceutical forms with different absorption rates, e.g. delayed-release forms compared with rapid-release forms. Various studies published in recent years verify that racemate preparations regarded as bioequivalent according to current criteria are no longer bioequivalent when the enantiomers are considered separately. For administration of the S(+) enantiomer, these findings, together with the simple pharmacokinetics and the patients' improved possibilities of stabilization, make a decisive contribution to the safety of chronic therapy.

In studies on animals, test subjects and patients, the S(+) enantiomer at a comparatively low dosage exhibited the same therapeutic action as the racemate. On rhesus monkeys, S(+)-ibuprofen was found to have a stronger analgesic action. In a skin inflammation model on healthy test subjects, the dose-effect curve of S(+)-ibuprofen was shifted towards lower dosage relative to that of the racemate. On arthritic patients, a good therapeutic effect was determined with a daily dose which was well below the conventional racemate dosage. These findings show that it is possible to achieve the same therapeutic activity with a lower dosage. This also contributes to the patients' safety.

Probably on the basis of these findings, European patent 267 321 describes a drug containing ibuprofen only as S(+)-ibuprofen with conventional excipients and binders, it being possible for said drug to be either in the delayed-release form or else in combination with non-delayed-release S(+)-ibuprofen. The delayed-release form, as a characterizing feature, was chosen because it had hitherto been impossible to provide the daily doses of the racemate of 1200 to 2400 mg in the bulky delayed-release forms. It was not until the daily doses could be reduced by using the S(+) enantiomer that the delayed-release forms, which were bulkier due to the adjuncts, coatings and the like, became applicable to the patient. Formulation to tablets, coated tablets and other formulations suitable for delayed release is carried out in conventional manner using the known excipients and adjuncts. The formulations known from pharmaceutics can also be used in this invention.

It is of great importance that analgesics start to take effect rapidly. U.S. Pat. No. 4,851,444 describes that the analgesic effect of S(+)-ibuprofen starts more rapidly and is more intense than that of identical amounts of the racemate. Said patent also claims a method of achieving a more rapid and more intense analgesic effect in humans, which consists in administering suitable amount of S(+)-ibuprofen essentially free of R(−)-ibuprofen. The appropriate formulations can again be taken from the state of the art. As only part of the R(−) enantiomer is converted in vivo to the active S(+) enantiomer when the racemate is used, it is obvious that, when using identical amounts of the S(+) enantiomer and the racemate, the S(+) enantiomer, which constitutes exclusively the active principle, has a more intense and more rapid action.

As described in European patent application 0 288 732, organic acids can be added in an amount of 5–50% in order to improve the solubility properties of spherical ACE inhibitors, beta blockers, Ca channel blockers and other pharmaceuticals in an amount of 3–60%. To achieve the same object, European patent application 0 308 665 proposes the addition to poorly water-soluble 5-aminosalicylic acid of basic adjuncts in the range of 0.5–3 molar, based on the 5-amino-salicylic acid, in order to form a water-soluble salt. Application of both these technical teachings inevitably gives rise again to bulky forms of administration, because the desire for complete salt formation must involve molar equivalents.

Accordingly, the object of the invention was to provide rapid-release S(+)-ibuprofen drugs containing the smallest possible amounts of adjuncts. The first stage entailed building up pellets containing S(+)-ibuprofen.

Attempts in this direction were initially unsuccessful. With customary pelleting auxiliaries such as Avicel, lactose, Primojel and HPMC in various combinations with an active substance content of between 90 and 94%, the pellets were practically insoluble or only very poorly soluble in artificial intestinal juice. Surfactants were also added to improve the wetting; similarly, the hydrophilic substance PEG was also added to promote the water solubility. No acceleration of the release of the active substance in artificial intestinal juice could be found (cf. Comparative Examples A.–F.).

No improvement in the release of the active substance from the pellets could be observed even after increasing the pelleting adjuncts to 25 to 30%. Moreover, this naturally meant a corresponding reduction in the active substance content of the pellets, which was contrary to the object of the invention. Pharmaceutical forms capable of being swallowed, containing up to 600 mg of active substance, could not be produced with such pellets—whether they be filled into capsules or compressed to tablets.

It has now been found, surprisingly, that the addition of small non-equimolar amounts of a basic salt or a base makes it possible to form pellets containing a high concentration of S(+)-ibuprofen which release the active substance very rapidly under the conditions of USP XXII (phosphate buffer, pH 7.2).

Said pellets contain 90.0–99.0% by weight of S(+)-ibuprofen and 0.1–10.0% by weight of a basic inorganic salt or a dilute alkali metal hydroxide solution.

Preferably, the pellets contain 96.0–98.0% by weight, especially 97% by weight, of S(+)-ibuprofen and 1.0–3.0% by weight, especially 2.0% by weight, of a basic inorganic salt or a dilute alkali metal hydroxide solution.

Suitable basic inorganic salts are preferably sodium carbonate, potassium carbonate and disodium hydrogen phosphate and suitable bases are sodium hydroxide solution and potassium hydroxide solution, or mixtures thereof in each case.

The pellets can contain 0.1–5.0, especially 2.0% by weight, of at least one adjunct such as microcrystalline cellulose, lactose, hydroxypropyl methyl cellulose (HPMC) and/or, preferably, silicon dioxide.

A preferred embodiment of the pellets contains 90% by weight to 99% by weight, preferably 97% by weight, of S(+)-ibuprofen, 0.1% by weight to 5.0% by weight, preferably 1.0% by weight, of silicon dioxide and 0.1% by weight to 10.0% by weight, preferably 2.0% by weight, of sodium carbonate.

As well as improving the solubility properties, the effect of adding the basic inorganic salt or dilute alkali metal hydroxide solution during the pelleting process is to dissolve the S(+)-ibuprofen to a small extent, making the latter slightly sticky and thereby obviating the need to use additional binders.

The pellets can be prepared under mild conditions particularly in a rotary processor, e.g. the one marketed by Niro-Aeromatic, Bubendorf, Switzerland, or in a high-speed mixer, e.g. a Diosna mixer sold by Dierks und Söhne, Osnabrück, Germany.

Pellets can be prepared by spraying the mixture containing S(+)-ibuprofen and at least one adjunct, in the rotary processor or Diosna mixer, with a basic inorganic salt in aqueous solution or with a dilute alkali metal hydroxide solution. The pellets formed are dried and optionally fractionated. This procedure gives pellets of excellent roundness and high compactness, from which 90% is released within 20 minutes under the conditions of USP XXII, page 1784/85 (phosphate buffer, pH 7.2).

The pellets can optionally be provided with a coating. The purpose of the coating is to improve the handling of the pellets when they are filled into the hard gelatin capsules and/or to delay the release of the active substance. In particular, the coated pellets can be compressed directly to tablets with small amounts of suitable adjuncts; hitherto, with the pure active substance by itself, this could only be done with the aid of large amounts of tableting adjuncts (because of the considerable stickiness of the active substance at conventional processing temperatures) and, in some cases, technically expensive process steps (e.g. compression temperature <10° C. because of the low melting point of S(+)-ibuprofen). Furthermore, the tablets according to the invention have the advantage of masking the extremely soapy-bitter and lingering taste of S(+)-ibuprofen. The tablets can thus be taken and swallowed without reluctance or gustatory irritation with no need for an additional protective coating, as would otherwise be conventional for these tablets. Consequently, the active substance S(+)-ibuprofen, which is extremely difficult to process, can be processed via the pelleting operation described, in a simple tableting process which could not be carried out hitherto, to give compact rapid-release tablets in which the taste is also advantageously masked.

Suitable protective coatings for the pellets can contain 0.1–10.0% by weight (the % by weight data always being based on the uncoated pellet weight), preferably 2.0% by weight, of hydroxypropyl methyl cellulose (HPMC), hydroxypropyl cellulose (HPC), polyvinylpyrrolidone (PVP), polyvinyl acetate (PVA), methyl cellulose (MC) or mixtures thereof, or 0.1–20% by weight, preferably 10% by weight, of a methacrylic acid and/or an ethyl acrylate (in suspension, 30% solids content) such as Eudragit L 30 D.

Suitable coatings resistant to gastric juice can contain 0.1–60.0% by weight, preferably 25.0% by weight, of a methacrylic acid and/or an ethyl acrylate (in suspension, 30% solids content) such as Eudragit L 30 D, hydroxypropyl methyl cellulose phthalate (HPMCP) and/or cellulose acetate-phthalate.

Suitable delayed-release coatings can contain 0.1–50.0% by weight, preferably 20.0% by weight, of an ethyl acrylate and/or methyl methacrylate (suspension, 30% solids content) such as Eudragit NE 30 D and/or Eudragit RS 30 D and/or Eudragit RL 30 D, and/or ethyl cellulose.

All coatings are applied with the conventionally required and known adjuncts and the appropriate technical means. For use in pharmaceuticals and for environmental protection, it is sensible to base all the working processes on purely aqueous working methods such as those already belonging to the present state of the art.

The various types of coating can be used by themselves or in any combination with one another. Thus a preferred protective coating contains a combination of HPMC or Eudragit L 30 D and talc, titanium dioxide and/or silicon dioxide and optionally antifoam emulsion, diethyl phthalate and/or polyethylene glycol (PEG), a preferred coating resistant to gastric juice contains a combination of Eudragit L 30 D, diethyl phthalate, silicon dioxide and optionally antifoam emulsion SE2, and a preferred delayed-release coating contains Eudragit RS 30 D, talc, diethyl phthalate and optionally antifoam emulsion SE2.

The adjuncts in a preferred protective coating are preferably present as a combination in the following amounts:
in the case of HPMC as the polymer:
0.1–8.0% by weight, especially 2.0% by weight, of talc;
in the case of Eudragit L 30 D as the polymer:
0.1–8.0% by weight, especially 0.4% by weight, of silicon dioxide, 0.1–8.0% by weight, especially 0.4% by weight, of titanium dioxide, 0.1–8.0% by weight, especially 0.2% by weight, of PEG as a plasticizer, and optionally 0.01–0.5% by weight, especially 0.04% by weight, of antifoam emulsion SE2.

The adjuncts in a preferred coating resistant to gastric juice are preferably present as a combination in the following amounts:
0.1–8.0% by weight, especially 3.0% by weight, of silicon dioxide, 0.1–8.0% by weight, especially 1.0% by weight, of diethyl phthalate as a plasticizer, and optionally 0.01–0.5% by weight, especially 0.04% by weight, of antifoam emulsion SE2.

The adjuncts in a preferred delayed-release coating are preferably present as a combination in the following amounts:
0.1–8.0% by weight, especially 3.0% by weight, of talc, 0.1–8.0% by weight, especially 1.0% by weight, of diethyl phthalate as a plasticizer, and optionally 0.01–0.5% by weight, especially 0.04% by weight, of antifoam emulsion SE2.

The coated pellets can be compressed to tablets by means of customary processes, said tablets containing 73–410 mg, preferably 240–260 mg and particularly preferably 250 mg, of at least one tableting auxiliary per 400 mg of S(+)-ibuprofen.

Suitable tableting auxiliaries are especially microcrystalline cellulose, calcium hydrogen phosphate such as Emcompress, lactose, starch such as corn starch, crosscarmellose sodium such as Ac-Di-Sol, sodium starch glycolate such as Primojel, PVP, HPMC, magnesium stearate, hydrogenated castor oil such as Cutina HR, silicon dioxide such as Aerosil 200, potassium chloride, calcium chloride, sodium chloride, sodium citrate, potassium adipate, calcium lactate and/or potassium citrate or mixtures thereof.

A preferred mixture of tableting auxiliaries contains a combination of microcrystalline cellulose, corn starch, PVP, magnesium stearate, silicon dioxide and potassium chloride.

The tablets can contain 50–800 mg, preferably 100–600 mg and particularly preferably 400 mg, of S(+)-ibuprofen. As tableting auxiliaries, a tablet containing 400 mg of S(+)-ibuprofen preferably contains 60 mg to 200 mg, particularly preferably 160 mg, of micro-crytalline cellulose, 10 mg to 80 mg, preferably 40 mg, of corn starch, 1 mg to 40 mg, preferably 14 mg, of PVP, 1 mg to 20 mg, preferably 8 mg, of magnesium stearate, 1 mg to 30 mg, preferably 14 mg, of silicon dioxide and 0.1 mg to 40 mg, preferably 15 mg, of potassium chloride.

The in vitro disintegration time, under the conditions of USP XXII, of a tablet according to the invention is less than 2 minutes and a tablet according to the invention has an active substance release, under the conditions of USP XXII, of over 90% of S(+)-ibuprofen within 20 minutes (USP XXII, p. 1784/85, phosphate buffer, pH 7.2).

The optionally coated pellets can also be filled into capsules. The high content of active substance, namely S(+) enantiomer, in relation to the adjuncts makes it possible, for example for 400 mg of S(+)-ibuprofen, to use size 0 capsules, which are most acceptable for swallowing.

By administering the pellets according to the invention to humans and animals, a saving of at least 25% in the amount of active substance can be made in comparison with the racemate for equivalent plasma levels.

The following Comparative Examples A–F describe unsuccessful pelleting experiments with customary adjuncts, while Examples 1–11 illustrate the invention in greater detail, the numerical data in the Comparative Examples and in the Examples always being in % by weight, unless indicated otherwise.

COMPARATIVE EXAMPLE A

| | |
|---|---|
| S(+)-Ibuprofen | 97.35 |
| Metolose 90SH 30000 (= hydroxypropyl methyl cellulose) | 0.15 |
| PEG 4000 | 2.00 |
| Tween 80 | 0.50 |
| Purified water | q.s. |

The active substance and the auxiliary substances are mixed. The water-soluble PEG and the Tween surfactant are admixed to improve the dissolution of the S(+)-ibuprofen. This mixture is sprayed with purified water in a Diosna mixer or a rotary processor in conventional manner until pellets of the desired size have been formed. The pellets are then dried and fractionated with a nutating sieve.

Figure 1:
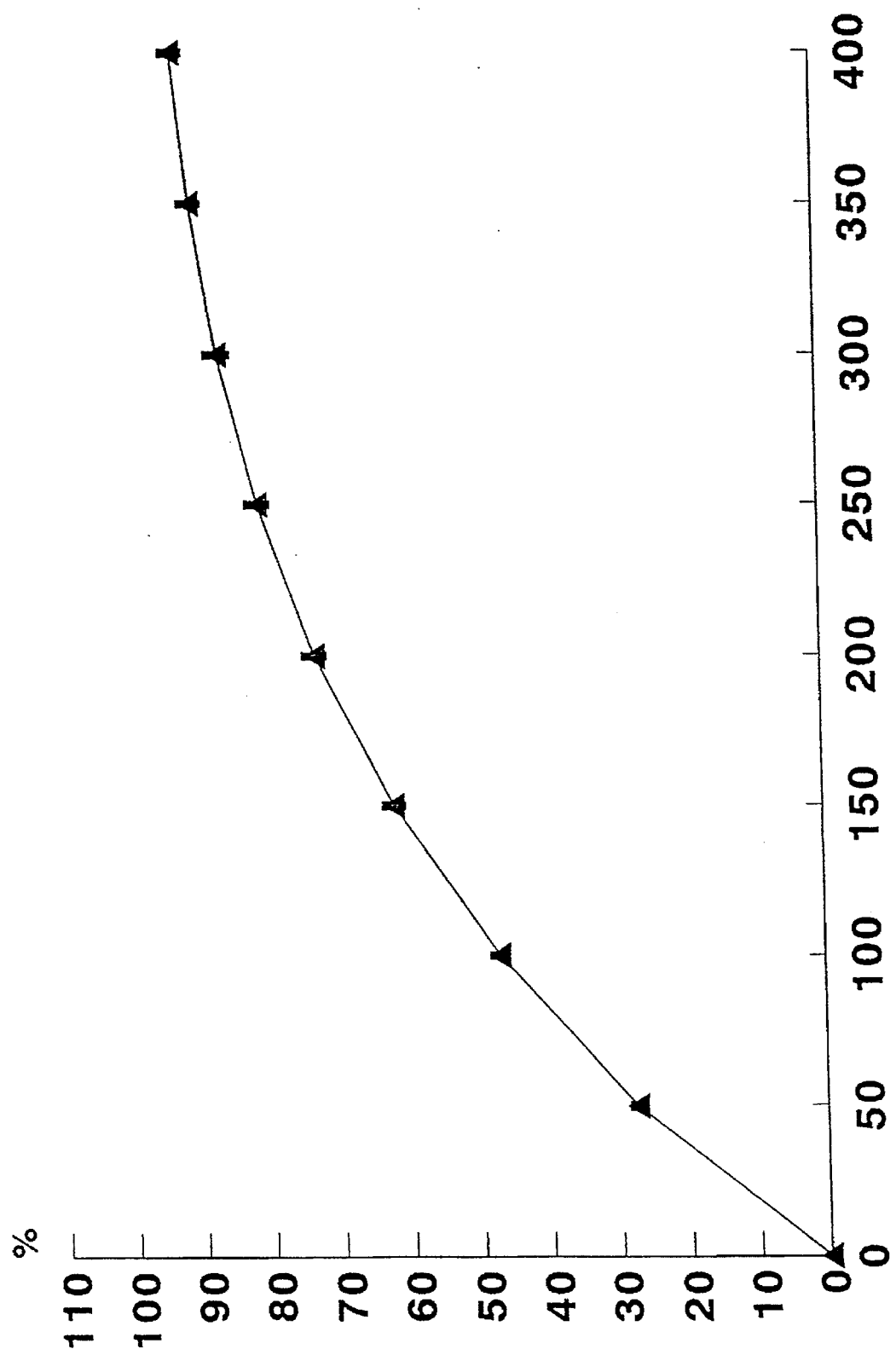
FIG. 1 shows the results of the in vitro release of the pellets of Example A under the conditions of USP XXII (phosphate buffer, pH 7.2).

The results of the in vitro release from the pellets under the conditions of USP XXII (phosphate buffer, pH 7.2) in FIG. 1 show the unsatisfactory dissolution behavior of these pellets.

COMPARATIVE EXAMPLE B

| | |
|---|---|
| S(+)-Ibuprofen | 95.00 |
| Microcrystalline cellulose | 1.5 |
| Pharmacoat 606 (= HPMC) | 1.00 |
| PEG 4000 | 2.0 |
| Tween 80 | 0.5 |
| Purified water | q.s. |

The active substance and the auxiliary substances are mixed. The water-soluble PEG and the Tween surfactant are admixed to improve the dissolution of the S(+)-ibuprofen. This mixture is sprayed with purified water in a Diosna mixer or a rotary processor in conventional manner until pellets of the desired size have been formed. The pellets are then dried and fractionated with a nutating sieve.

Figure 2:
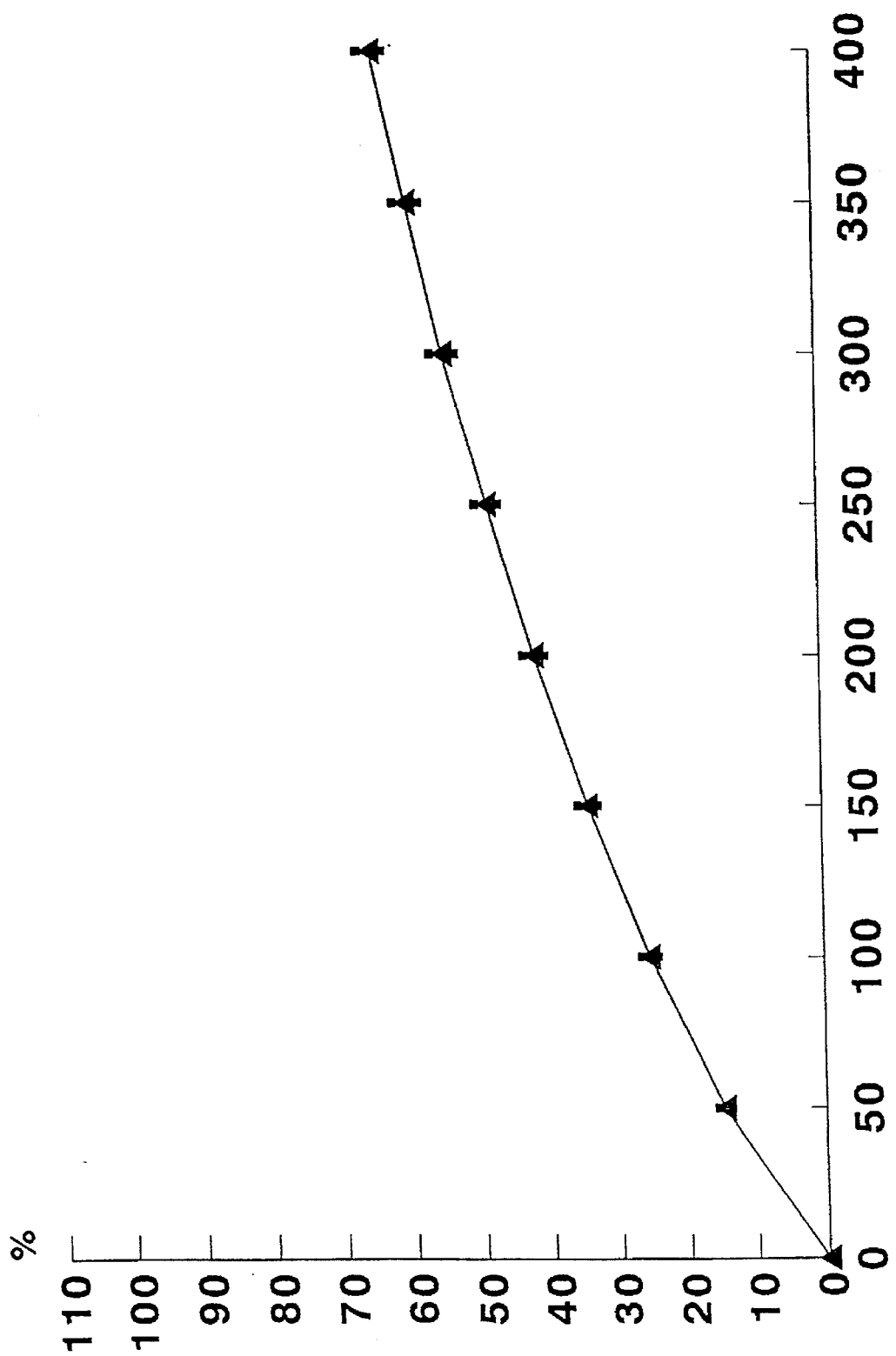
FIG. 2 shows the results of the in vitro release of the pellets of Example B under the conditions of USP XXII (phosphate buffer, pH 7.2).

The results of the in vitro release from the pellets under the conditions of USP XXII (phosphate buffer, pH 7.2) in FIG. 2 show the unsatisfactory dissolution behavior of these pellets.

COMPARATIVE EXAMPLE C

| | |
|---|---|
| S(+)-Ibuprofen | 90.00 |
| Microcrystalline cellulose | 4.5 |
| Pharmacoat 606 | 1.00 |
| PEG 4000 | 4.0 |
| Tween 80 | 0.5 |
| Purified water | q.s. |

The active substance and the auxiliary substances are mixed. The water-soluble PEG and the Tween surfactant are admixed to improve the dissolution of the S(+)-ibuprofen. This mixture is sprayed with purified water in a Diosna mixer or a rotary processor in conventional manner until pellets of the desired size have been formed. The pellets are then dried and fractionated with a nutating sieve.

Figure 3:
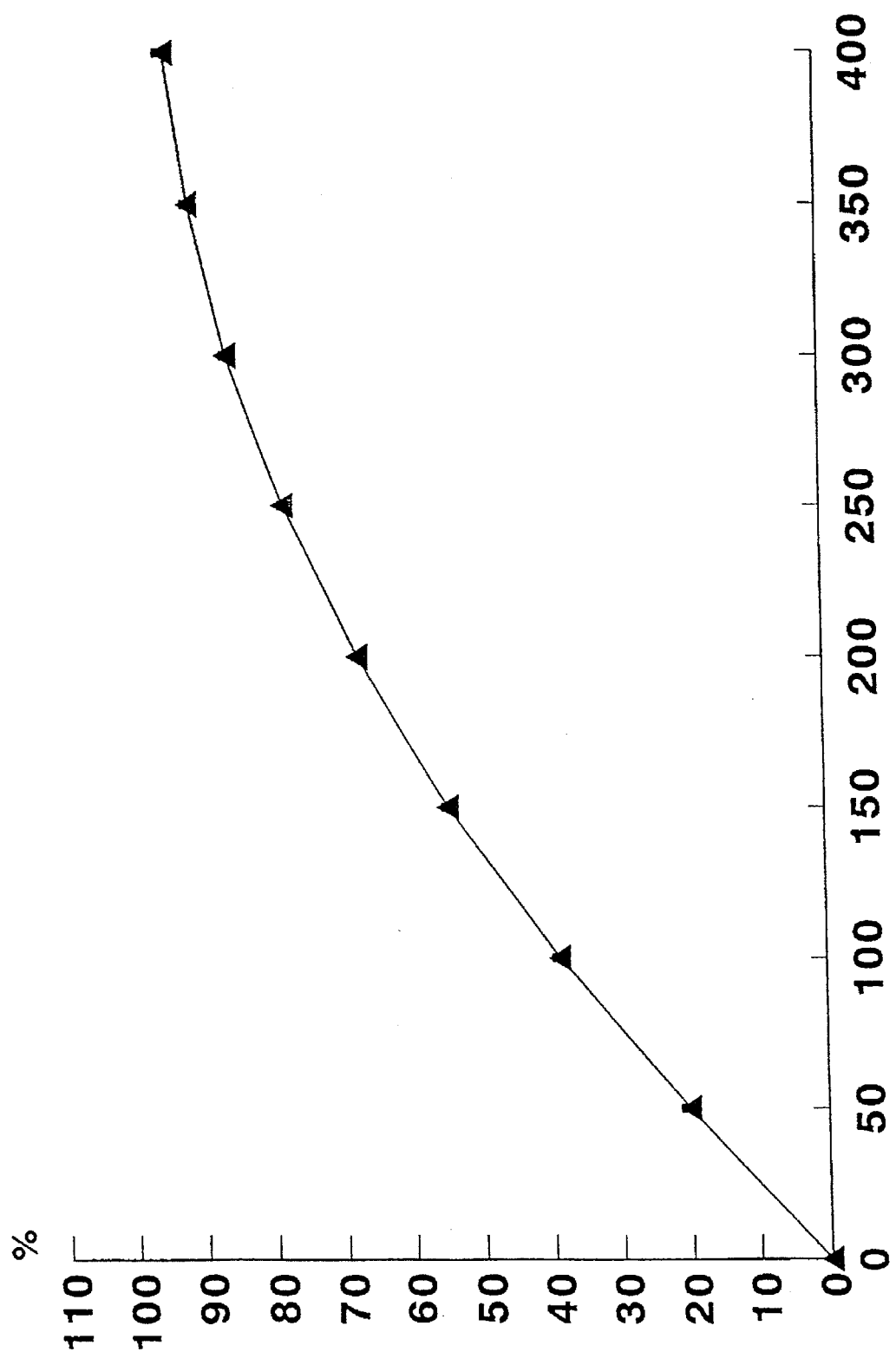
FIG. 3 shows the results of the in vitro release of the pellets of Example C under the conditions of USP XXII (phosphate buffer, pH 7.2).

The results of the in vitro release from the pellets under the conditions of USP XXII (phosphate buffer, pH 7.2) in FIG. 3 show the unsatisfactory dissolution behavior of these pellets.

COMPARATIVE EXAMPLE D

| | |
|---|---|
| S(+)-Ibuprofen | 70.00 |
| Microcrystalline cellulose | 15.00 |
| Lactose | 15.00 |
| Purified water | q.s. |

The active substance and the auxiliary substances are mixed. This mixture is sprayed with purified water in a Diosna mixer or a rotary processor in conventional manner until pellets of the desired size have been formed. The pellets are then dried and fractionated with a nutating sieve.

Figure 4:
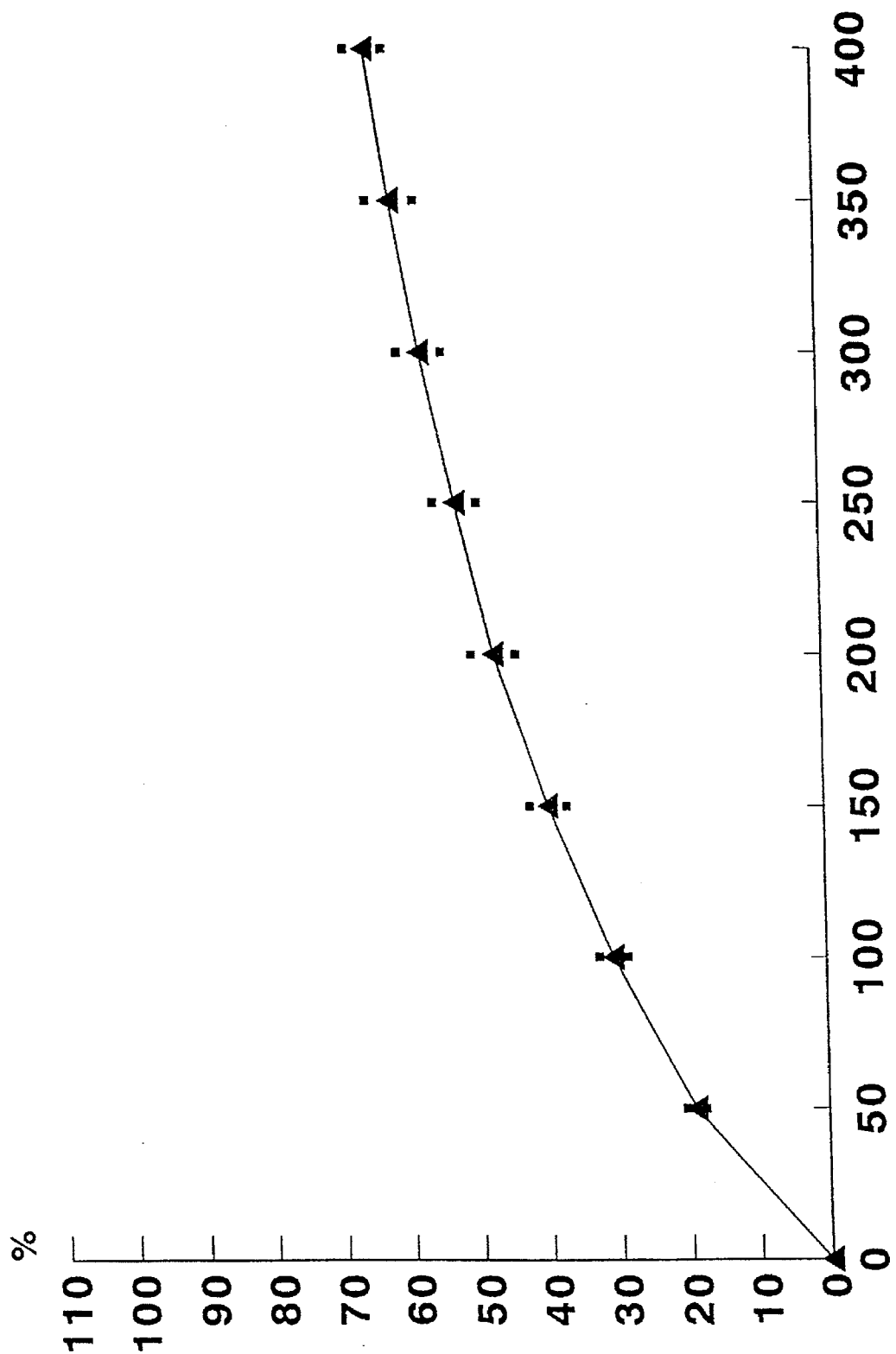
FIG. 4 shows the results of the in vitro release of the pellets of Example D uuder the conditions of USP XXII (phosphate buffer, pH 7.2).

The results of the in vitro release from the pellets under the conditions of USP XXII (phosphate buffer, pH 7.2) in FIG. 4 show the unsatisfactory dissolution behavior of these pellets, even though the proportion of adjuncts has been increased to 30%.

COMPARATIVE EXAMPLE E

| | |
|---|---|
| S(+)-Ibuprofen | 75.00 |
| Lactose | 15.00 |
| PEG 4000 | 10.00 |
| Purified water | q.s. |

The active substance and the auxiliary substances are mixed. This mixture is sprayed with purified water in a Diosna mixer or a rotary processor in conventional manner until pellets of the desired size have been formed. The pellets are then dried and fractionated with a nutating sieve.

Figure 5:
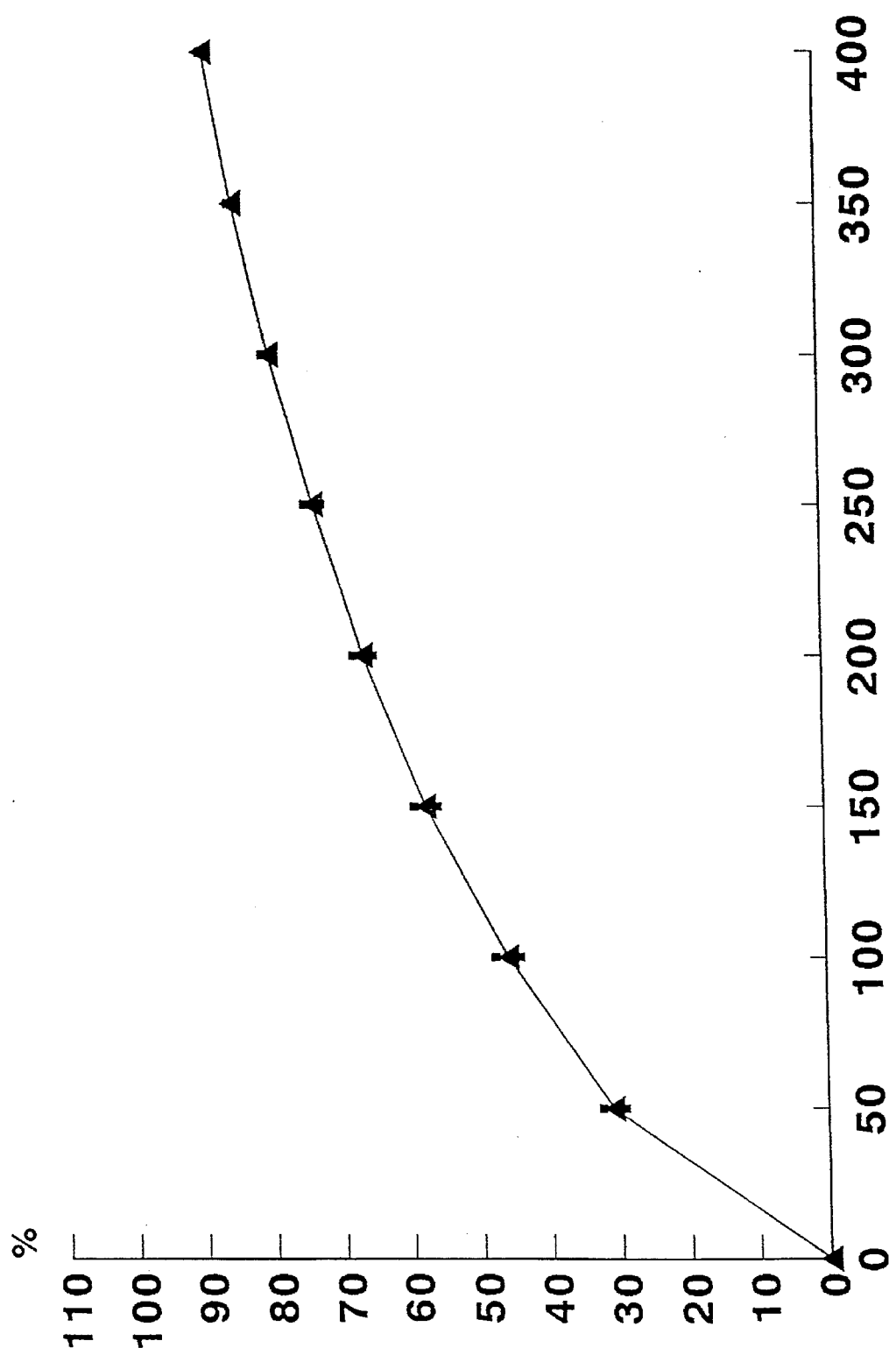
FIG. 5 shows the results of the in vitro release of the pellets of Example E under the conditions of USP XXII (phosphate buffer, pH 7.2).

The results of the in vitro release from the pellets under the conditions of USP XXII (phosphate buffer, pH 7.2) in FIG. 5 show the unsatisfactory dissolution behavior of these pellets, even though the proportion of adjuncts has been increased to 25%.

COMPARATIVE EXAMPLE F

| | |
|---|---|
| S(+)-Ibuprofen | 75.00 |
| Microcrystalline cellulose | 15.00 |
| PEG 4000 | 10.00 |
| Purified water | q.s. |

The active substance and the auxiliary substances are mixed. This mixture is sprayed with purified water in a Diosna mixer or a rotary processor in conventional manner until pellets of the desired size have been formed. The pellets are then dried and fractionated with a nutating sieve.

Figure 6:
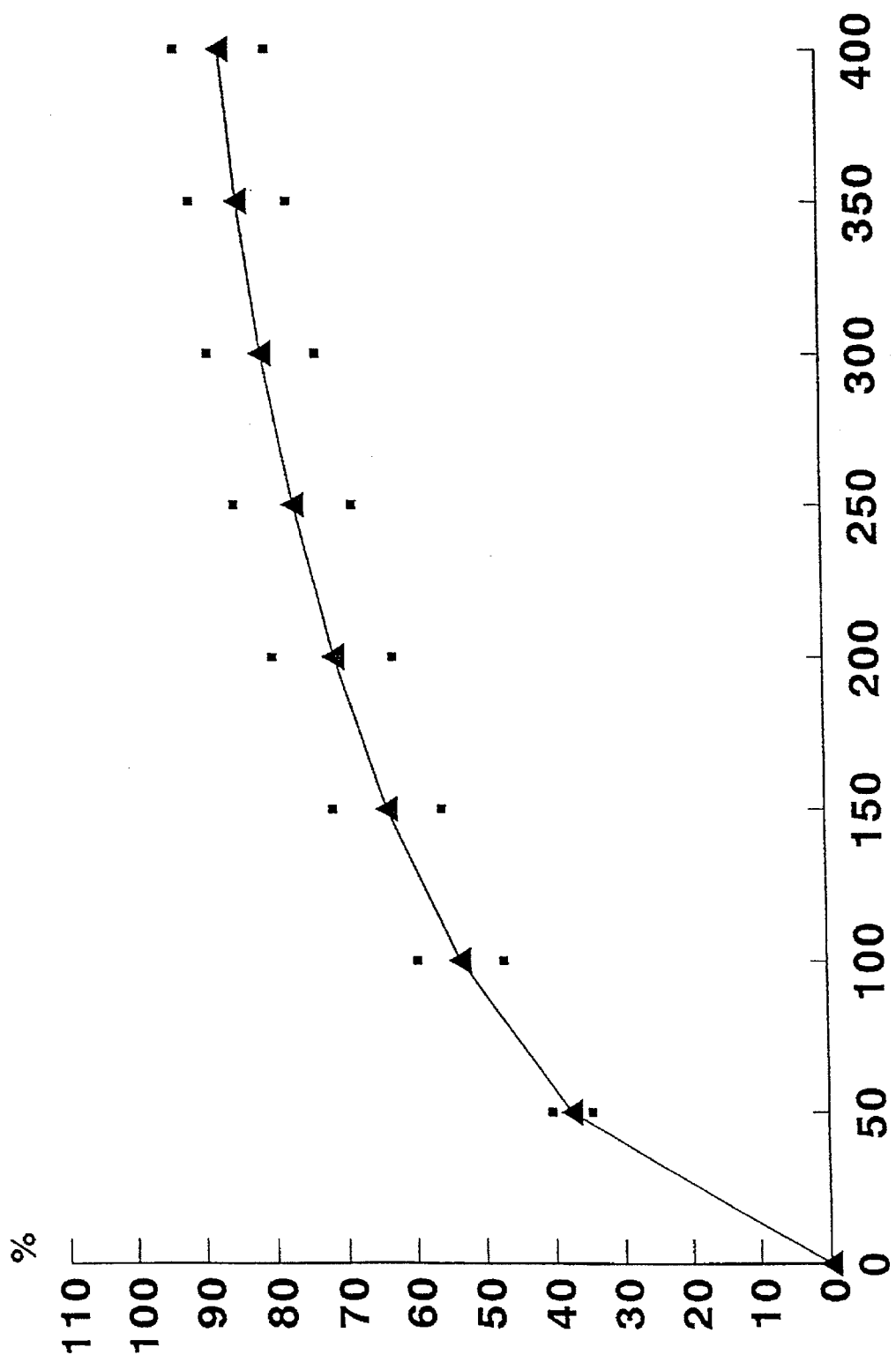
FIG. 6 shows the results of the in vitro release of the pellets of Example F under the conditions of USP XXII (phosphate buffer, pH7.2).

The results of the in vitro release from the pellets under the conditions of USP XXII (phosphate buffer, pH 7.2) in FIG. 6 show the unsatisfactory dissolution behavior of these pellets, even though the proportion of adjuncts has been increased to 25%.

Example 1

| | |
|---|---|
| S(+)-Ibuprofen | 95.0 |
| Sodium carbonate | 2.0 |
| HPMC | 3.0 |
| Purified water | q.s. |

The S(+)-ibuprofen, sodium carbonate and HPMC are mixed. This mixture is sprayed with purified water in a Diosna mixer or a rotary processor in conventional manner until pellets of the desired size have been formed. The pellets are then dried and fractionated with a nutating sieve.

Figure 7:
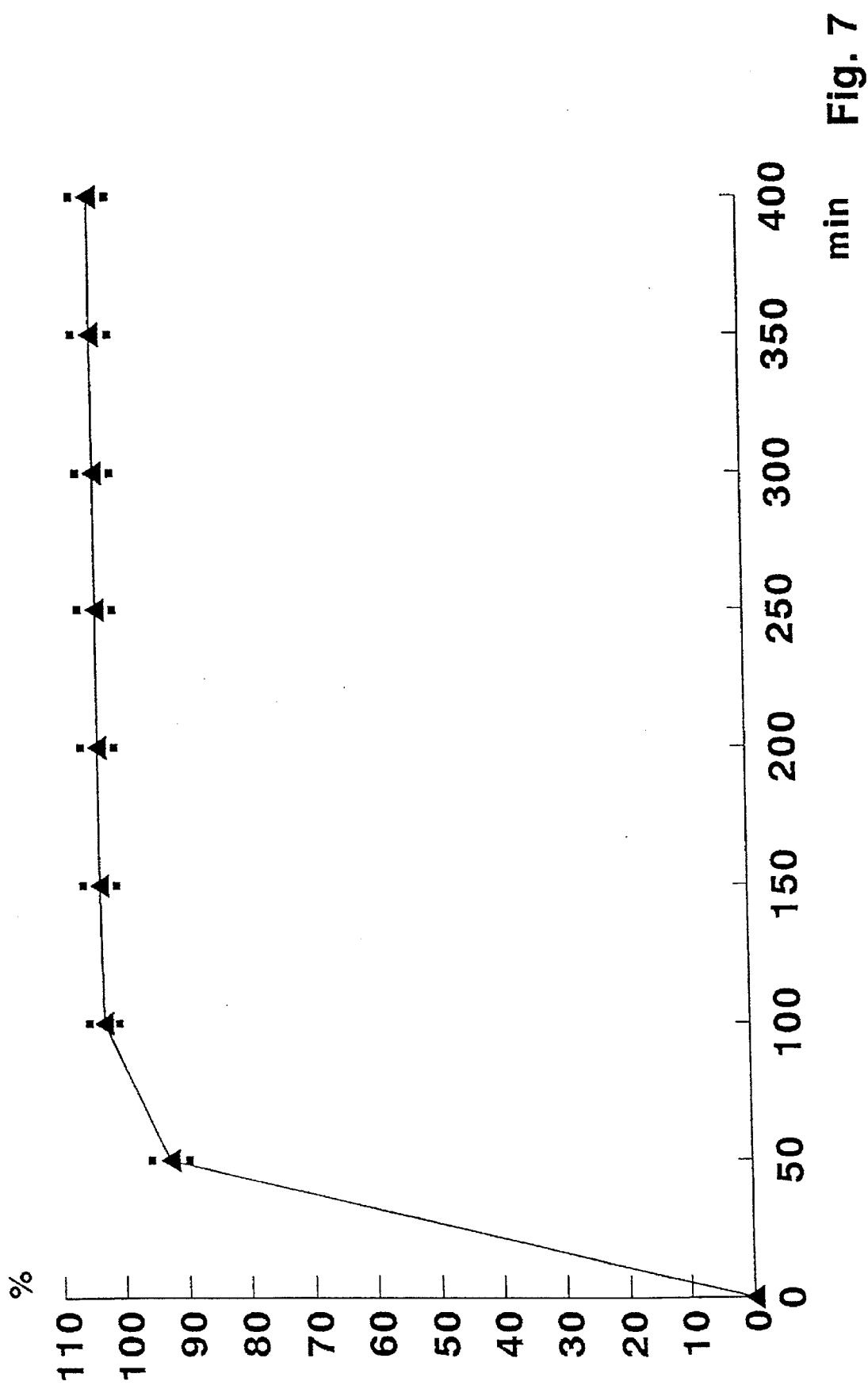
FIG. 7 shows the substantially accelerated release from the pellets of Example 1 under the conditions of USP XXII (phosphate buffer, pH 7.2), including the substantially more rapid course of release with a proportion of adjuncts of 5%.

This formulation achieved a breakthrough to substantially accelerated release from the pellets under the conditions of USP XXII (phosphate buffer, pH 7.2). FIG. 7 shows the substantially more rapid course of the release with a proportion of adjuncts of only 5%.

Example 2

| | |
|---|---|
| S(+)-Ibuprofen | 97.0 |
| Silicon dioxide | 1.0 |
| Sodium carbonate | 2.0 |
| Purified water | q.s. |

The S(+)-ibuprofen, silicon dioxide and sodium carbonate are mixed. This mixture is sprayed with purified water in a Diosna mixer or a rotary processor in conventional manner until pellets of the desired size have been formed. The pellets are then dried and fractionated with a nutating sieve.

With this formulation, over 90% of S(+)-ibuprofen can be released under the conditions of USP XXII (phosphate buffer, pH 7.2) with a proportion of adjuncts of only 3%.

Example 3

| | |
|---|---|
| S(+)-Ibuprofen | 90.0 |
| Microcrystalline cellulose | 4.0 |
| Lactose | 4.0 |
| Potassium hydroxide 10% | 20.0 |
| Purified water | q.s. |

The S(+)-ibuprofen, microcrystalline cellulose and lactose are mixed. This mixture is sprayed with potassium hydroxide and then with purified water in a Diosna mixer or a rotary processor until pellets of the desired size have been formed. The pellets are dried and fractionated with a nutating sieve.

Example 4

| | |
|---|---|
| S(+)-Ibuprofen | 92.0 |
| Microcrystalline cellulose | 5.0 |
| HPMC | 1.0 |
| Disodium hydrogen phosphate | 3.0 |
| Purified water | q.s. |

The S(+)-ibuprofen, microcrystalline cellulose, HPMC and disodium hydrogen phosphate are mixed. This mixture is sprayed with purified water in a Diosna mixer or a rotary processor until pellets of the desired size have been formed. The pellets are dried and fractionated with a nutating sieve.

Example 5

(coating resistant to gastric juice)

| | |
|---|---|
| S(+)-Ibuprofen pellets | 100.0 |
| Purified water | 12.3 |
| Antifoam emulsion SE2 | 0.04 |
| Silicon dioxide | 3.0 |
| Diethyl phthalate | 1.0 |
| Eudragit L 30 D | 25.0 LS = 11.25% |

(LS = lacquer solids)

The antifoam emulsion and silicon dioxide are suspended in purified water and then slowly stirred, together with the diethyl phthalate, into the Eudragit. The pellets are sprayed with the suspension in a fluidized bed granulator (FBG).

Example 6

(protective coating)

| | |
|---|---|
| S(+)-Ibuprofen pellets | 100.0 |
| HPMC | 2.0 |
| Talc | 2.0 |
| Purified water | 22.0 LS = 4.0% |

The HPMC and talc are suspended in purified water. The pellets are sprayed with this suspension in an FBG.

Example 7

(delayed-release pellets)

| | |
|---|---|
| S(+)-Ibuprofen pellets | 100.0 |
| Purified water | 26.0 |
| Antifoam emulsion SE2 | 0.02 |
| Talc | 3.0 |
| Diethyl phthalate | 1.0 |
| Eudragit RS 30 D | 20.0 LS = 10.0% |

The talc and antifoam emulsion are suspended in purified water. This suspension and the diethyl phthalate are then stirred into the Eudragit, after which the pellets are sprayed with the above suspension in an FBG.

Example 8

(data per tablet in mg)

| | |
|---|---|
| S(+)-Ibuprofen pellets, coated (93.2% AS) | 429.0 |
| Microcrystalline cellulose | 160.0 |
| Corn starch | 40.0 |
| Potassium chloride | 15.0 |
| PVP | 14.0 |
| Magnesium stearate | 6.0 |
| Silicon dioxide | 14.0 |

(AS = active substance)

(AS = active substance)

The mixture is compressed directly to tablets. The tablets disintegrate within 2 minutes (under the conditions of USP XXII, p. 1577) and show an active substance release of over 90% of S(+)-ibuprofen within 20 minutes under the conditions of USP XXII, p. 1578 (phosphate buffer, pH 7.2).

The following auxiliary substances can be used as alternatives to potassium chloride or else in combination therewith:

sodium chloride, calcium chloride, sodium citrate, potassium hydrogen phosphate, potassium adipate, calcium lactate and potassium citrate.

For 50 mg, 100 mg, 200 mg, 600 mg and 800 mg tablets, the components are calculated in proportion to the above data.

Example 9

(data per tablet in mg)

| | |
|---|---|
| S(+)-Ibuprofen pellets, coated (93.2% AS) | 429.0 |
| Emcompress | 140.0 |
| Ac-Di-Sol | 50.0 |
| HPMC | 20.0 |
| Cutina HR | 8.0 |
| Silicon dioxide | 10.0 |

Figure 8:
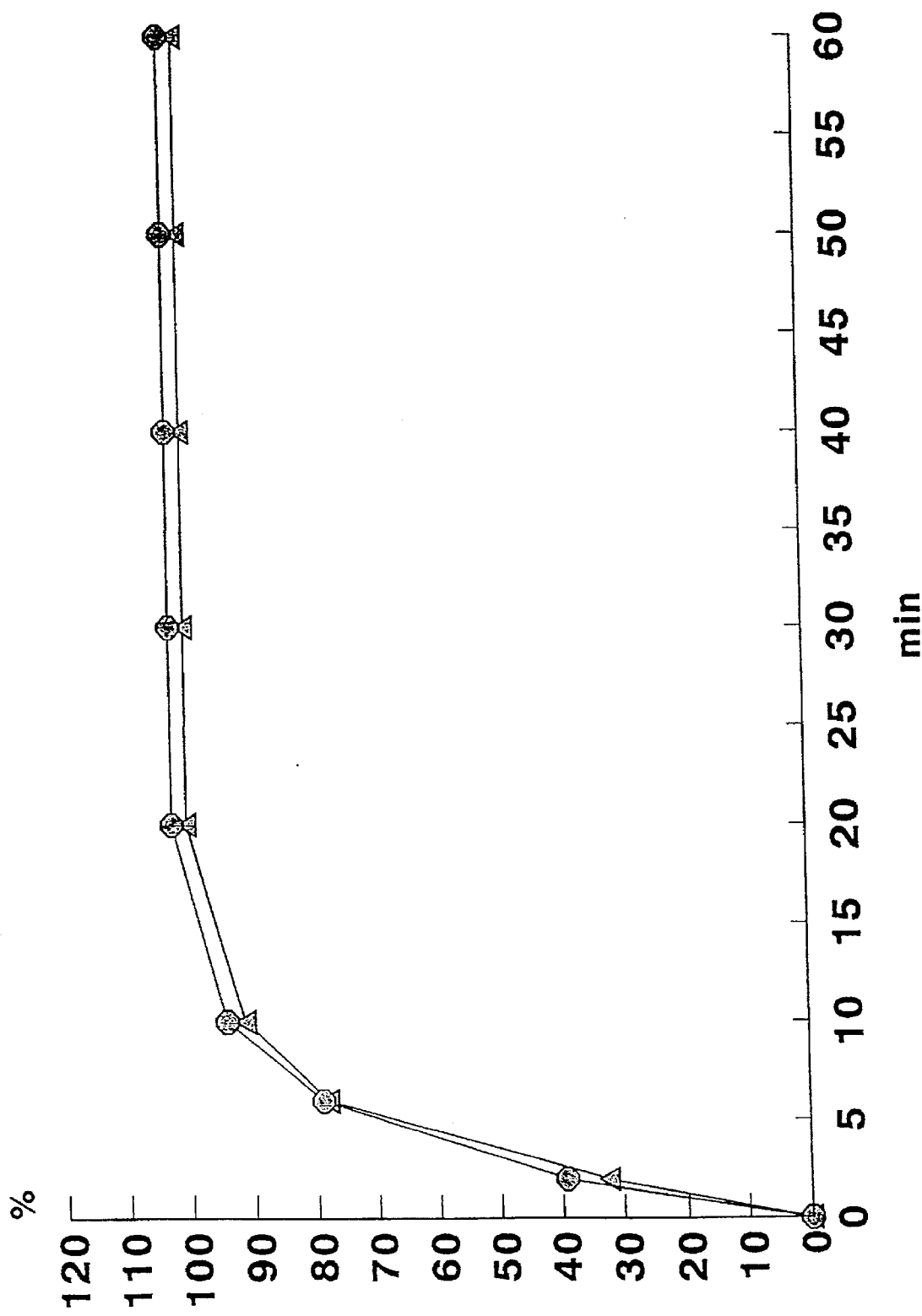
FIG. 8 shows active substance release from the pellets of Example 9 of >90% in less than 20 minutes.

The mixture is compressed directly to tablets in customary manner. In the test with 2 different batches, the active substance release is again >90% in less than 20 minutes under the conditions of USP XXII (phosphate buffer, pH 7.2) (FIG. 8).

Example 10

(pellets filled into capsules)

| | |
|---|---|
| S(+)-Ibuprofen pellets, (uncoated 97% AS) | 413.0 |

The pellets prepared according to Example 2 are filled into size 0 hard gelatin capsules on a capsule filling machine.

The active substance release from these pellets under the above-mentioned conditions (USP XXII, phosphate buffer, pH 7.2) again gives values for S(+)-ibuprofen of >90% within 20 minutes.

Example 11

Figure 9:
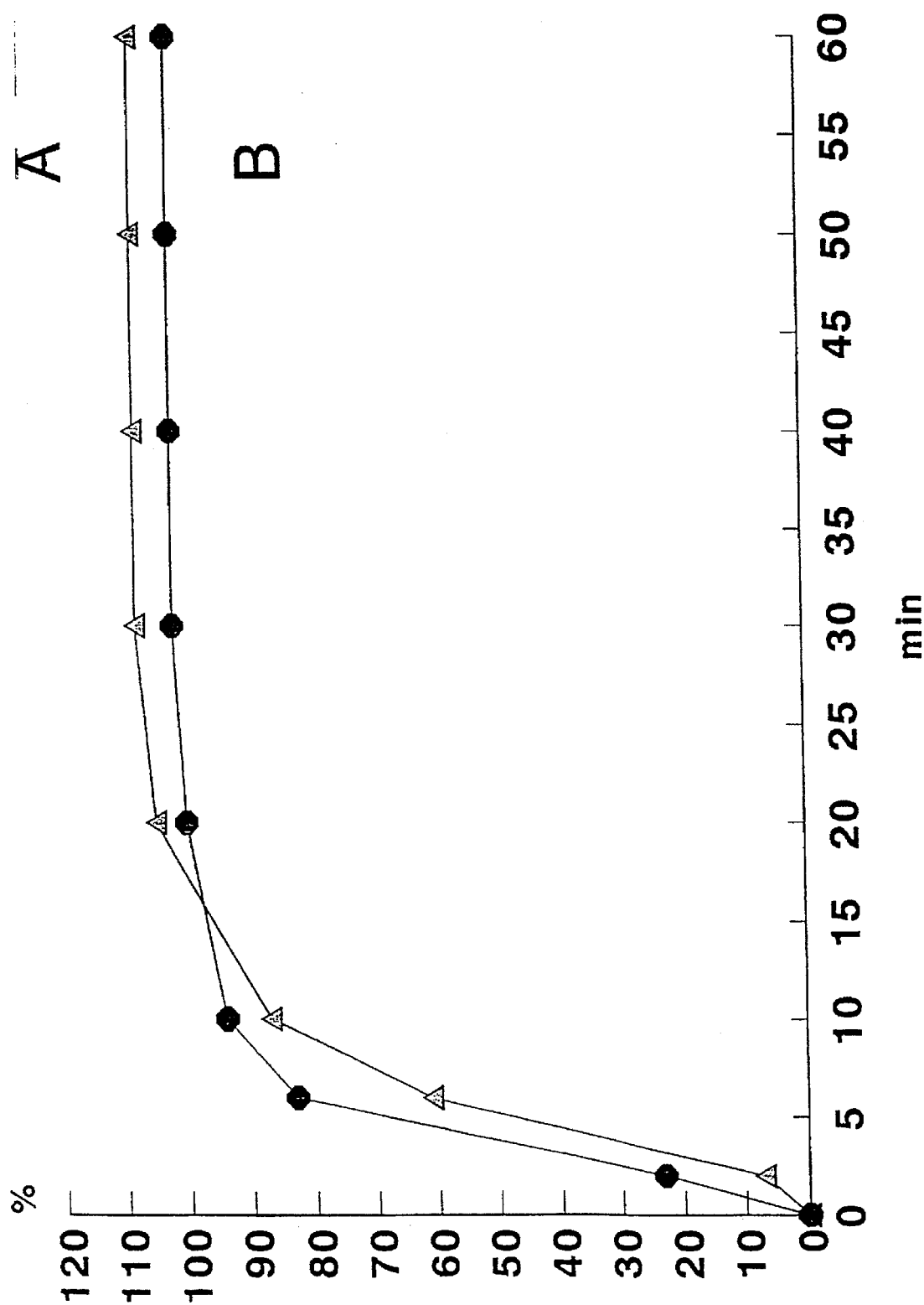
FIG. 9 shows the release from 200 mg tablets of Example 11 immediately after preparation (curve A) and 3 months later (curve B).
Figure 10:
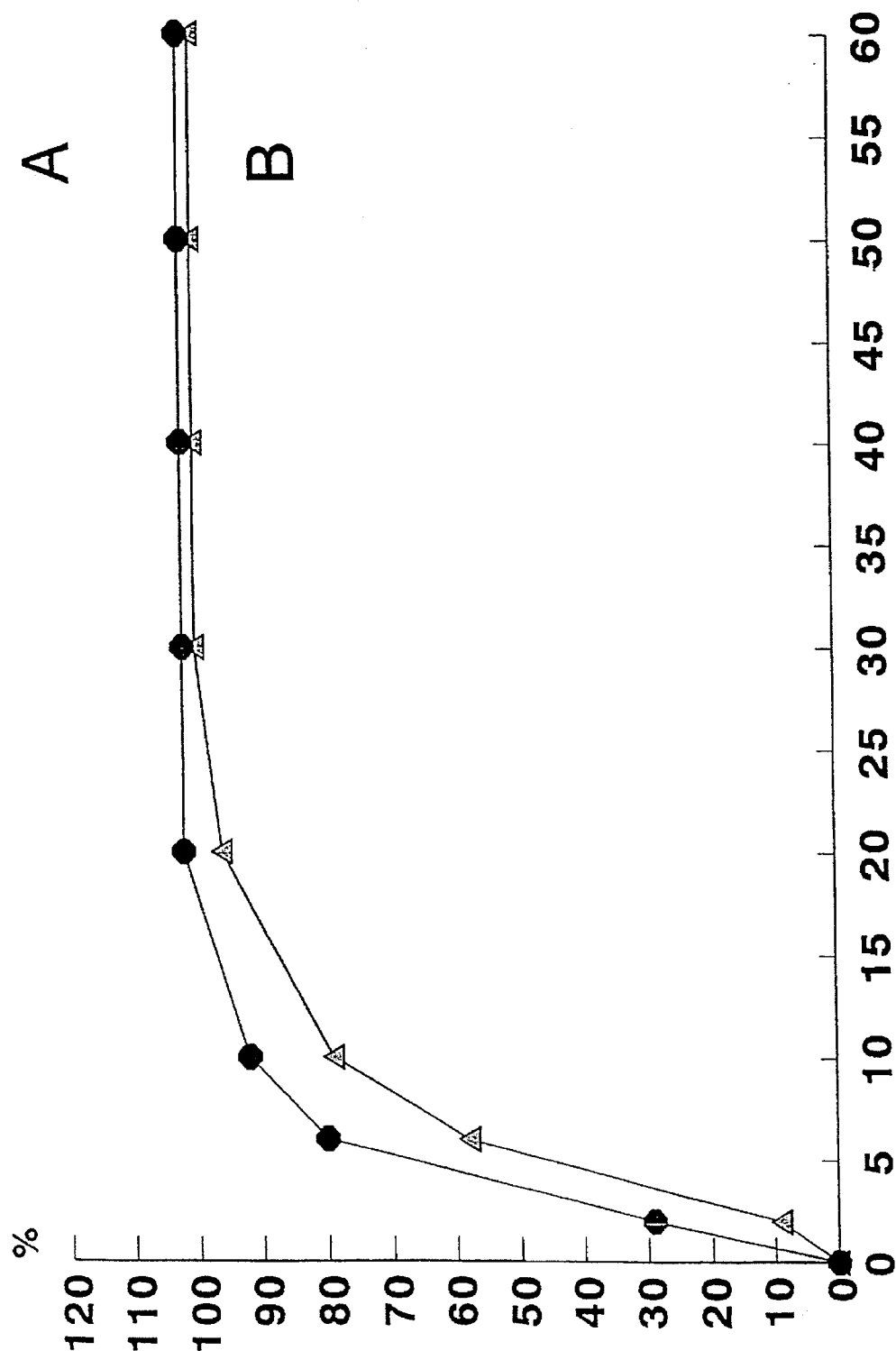
FIG. 10 shows the release from 400 mg tablets of Example 11 immediately after preparation (curve A) and 3 months later (curve B).
Figure 11:
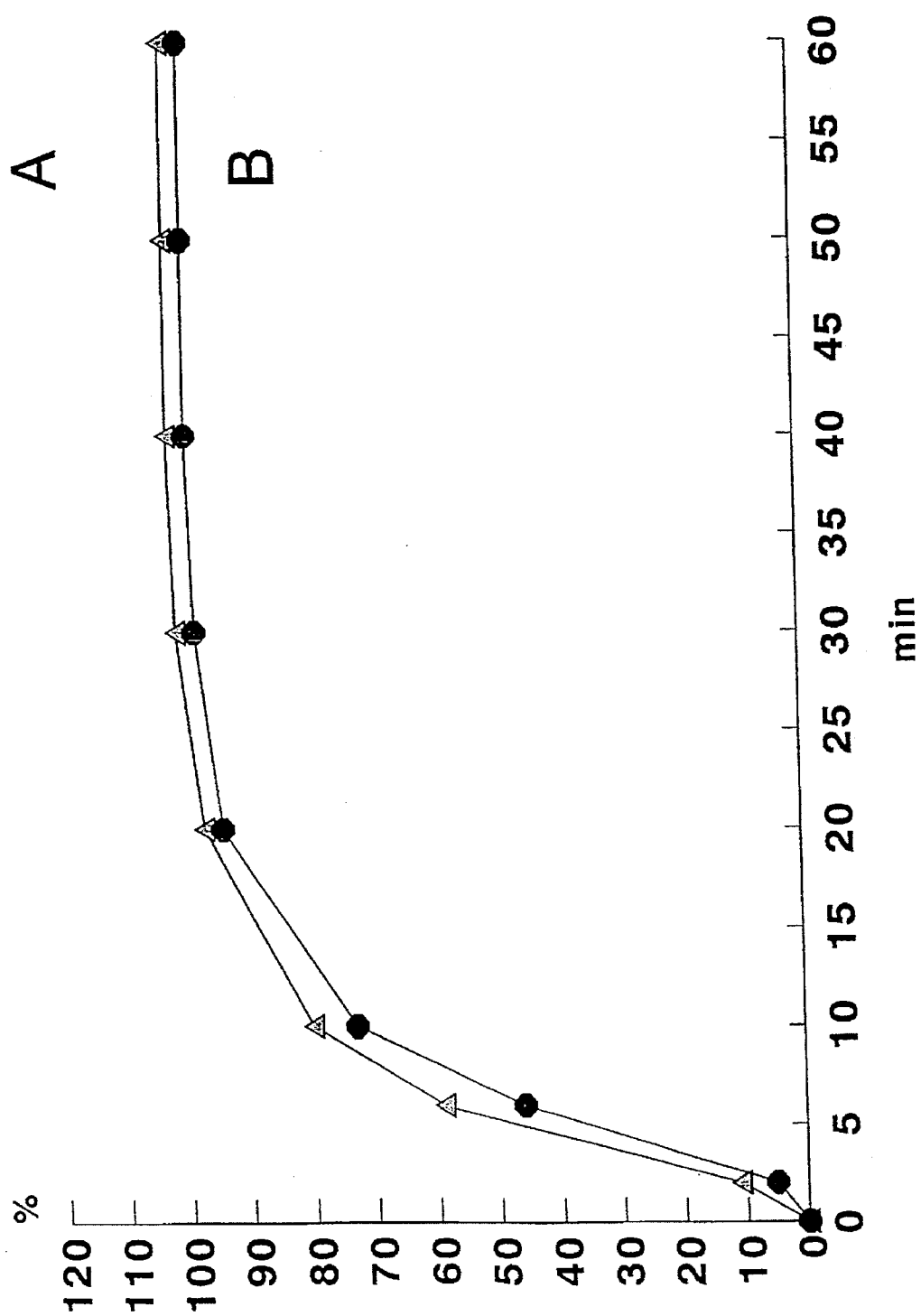
FIG. 11 shows the release from 600 mg tablets of Example 11 immediately after preparation (curve A) and 3 months later (curve B).

The in vitro release under the conditions of USP XXII (phosphate buffer, pH 7.2) from tablets according to the invention prepared according to Example 8, the corresponding pellets having been prepared according to Example 2 and coated analogously to Example 5, is represented graphically in FIG. 9–11.

The coating had the following composition in this case:

| | |
|---|---|
| S(+)-Ibuprofen | 100.0 |
| Purified water | 18.9 |
| Antifoam emulsion SE2 | 0.04 |
| Silicon dioxide | 0.4 |
| Titanium dioxide | 0.4 |
| Eudragit L 30 D | 10.0 |

FIG. 9 shows the release from 200 mg tablets immediately after preparation (curve A) and 3 months later (storage at 25° C. and 60% relative humidity; curve B). FIG. 10 and 11 show this for the 400 mg and 600 mg tablets respectively.

The curves show inter alia that the release of the active substance does not change significantly with storage.

Example 12

The bioavailability of S(+)-ibuprofen in the form of the pellets according to the invention in 200 mg capsules and of the pellets according to the invention in 200 mg, 400 mg and 600 mg tablets was compared with that of ibuprofen racemate in the form of the commercially available 400 mg, 800 mg and 1200 mg Brufen coated tablets. The test was carried out on 18 test subjects, who were given, on 3 different days, either 1, 2 or 3 pellet-filled capsules containing 200 mg of S(+)-ibuprofen, or in each case one tablet containing 200 mg, 400 mg or 600 mg of S(+)-ibuprofen, or in each case 1, 2 or 3 coated tablets containing 400 mg of ibuprofen racemate. The results are shown in FIG. 12–17.

Figure 12:
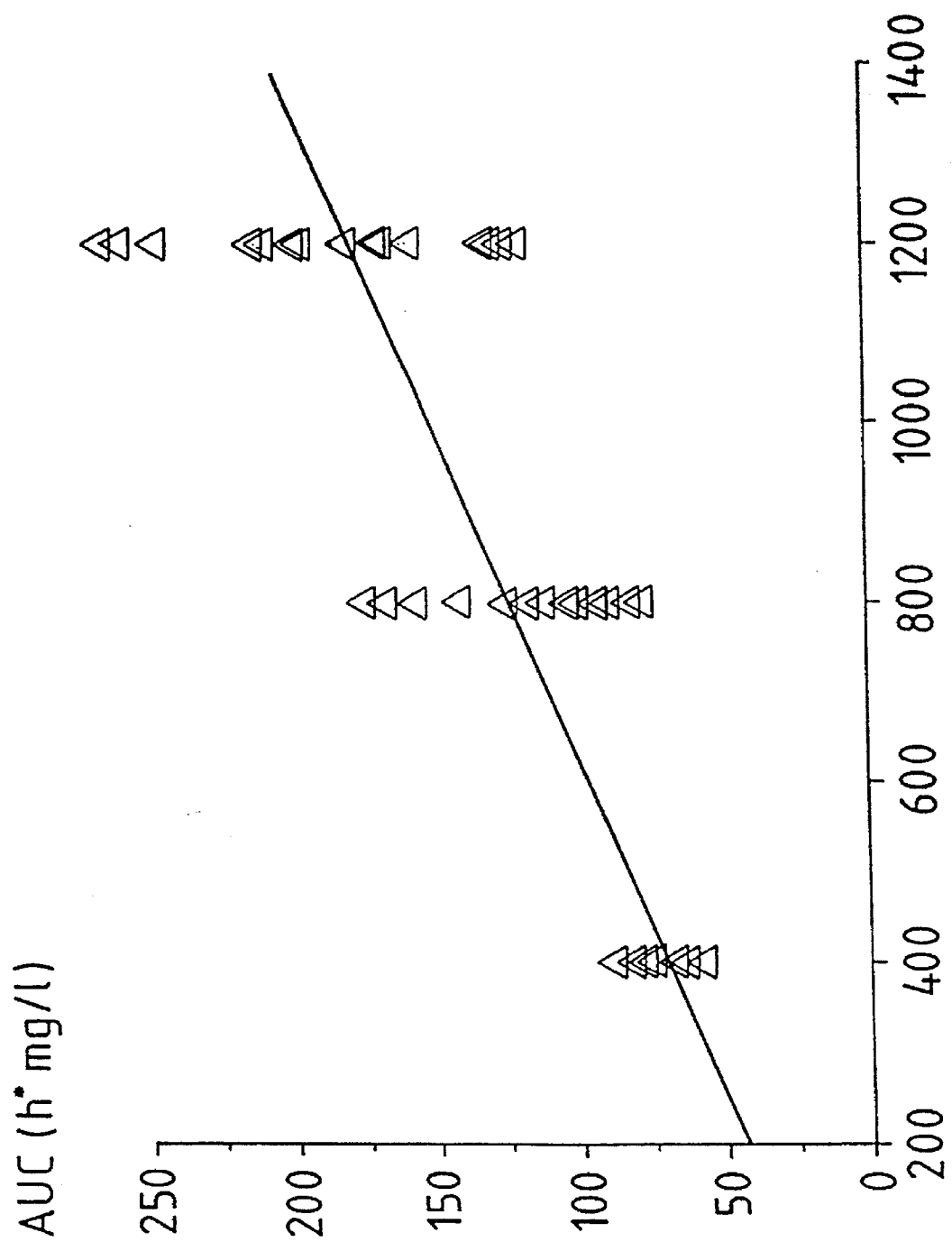
FIG. 12 shows the mean of the ratio of the measured amounts of S(+)-ibuprofen in a subject's plasma to the dose of the racemate given according to Example 12.
Figure 13:
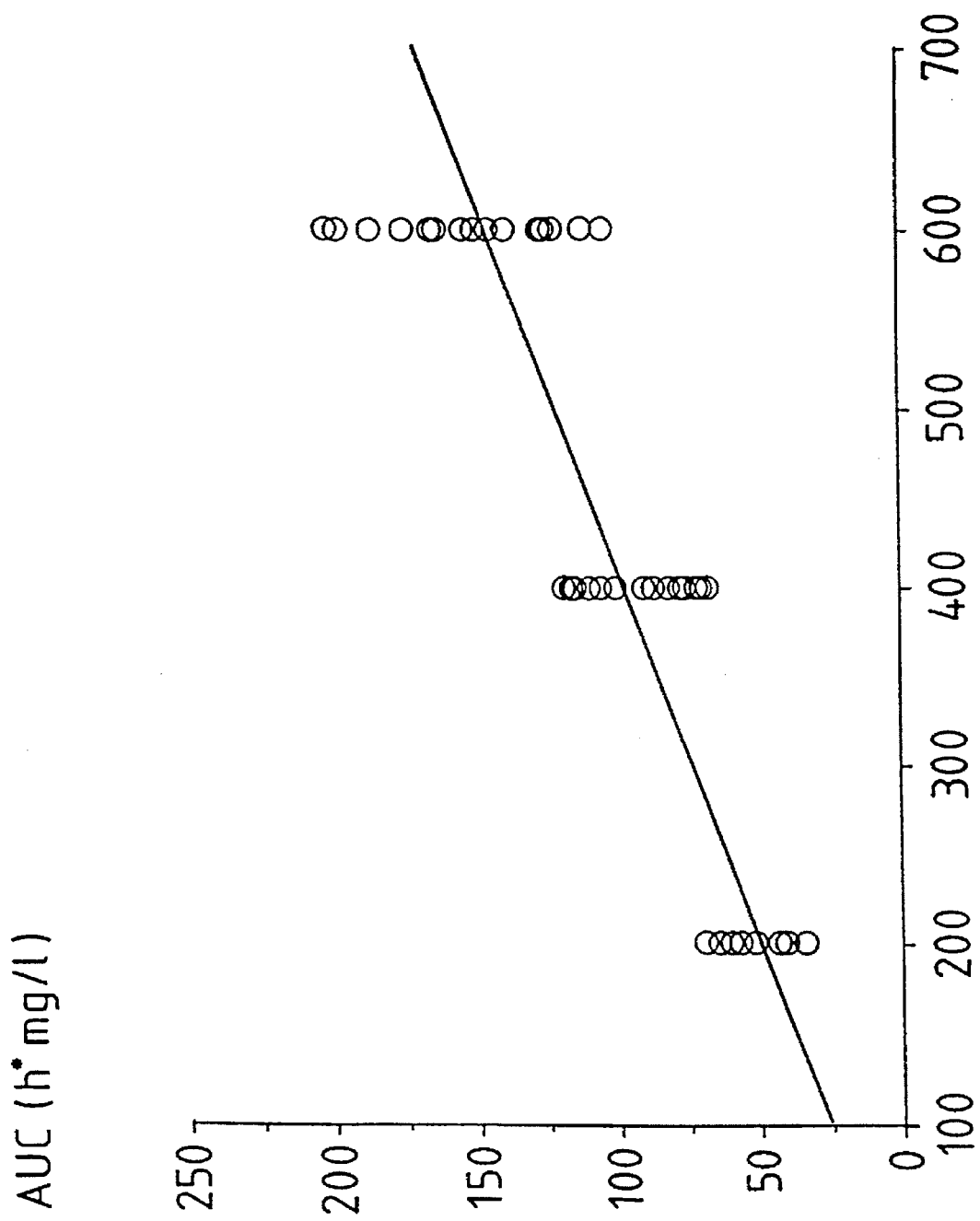
FIG. 13 shows the mean of the ratio of the measured amounts of S(+)-ibuprofen in the subject's plasma to the dose of the racemate given in capsule form according to Example 12.
Figure 14:
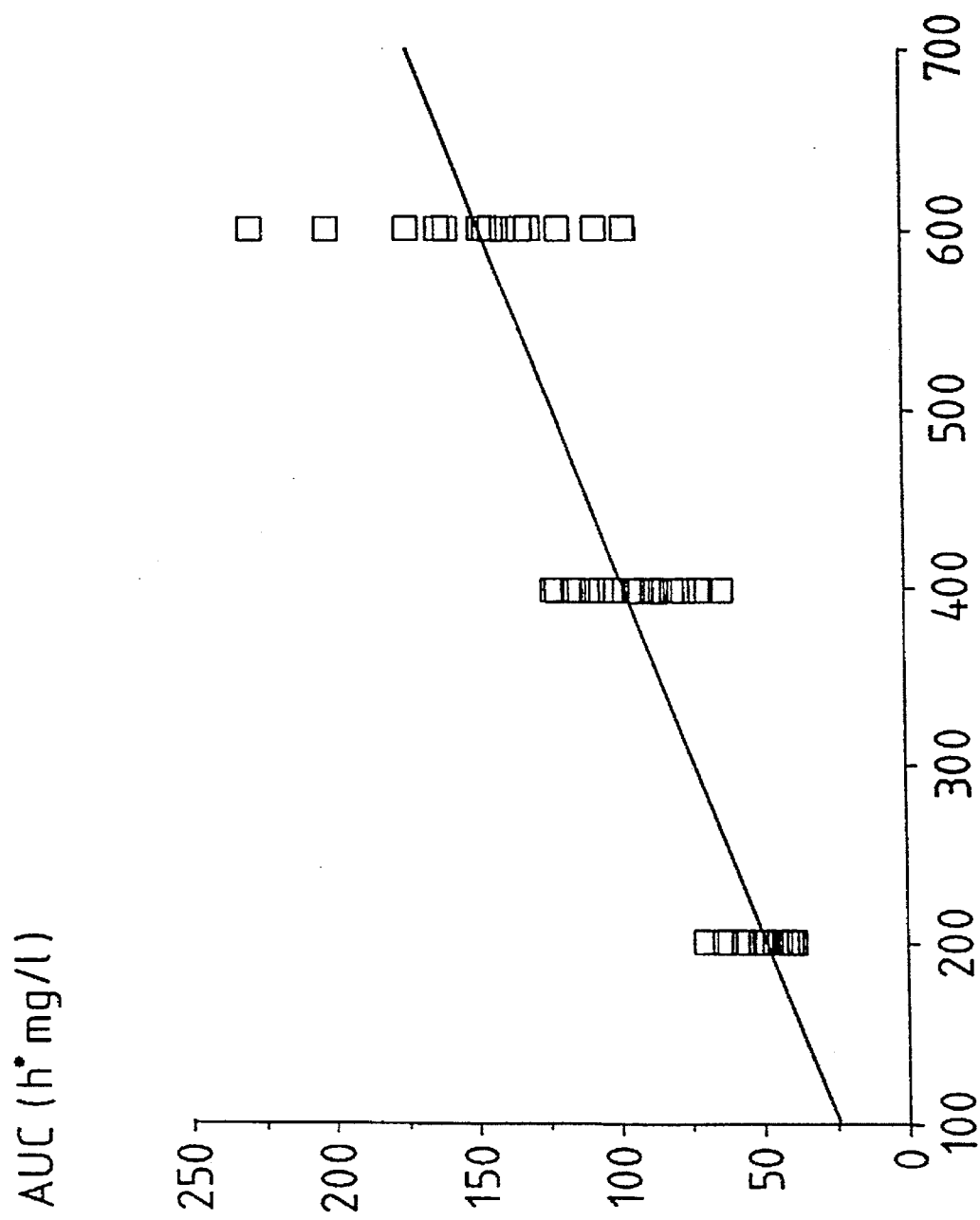
FIG. 14 shows the mean of the ratio of the measured amounts of S(+)-ibuprofen in the subject's plasma to the dose of the racemate given in capsule form accordinging to Example 12.
Figure 15:
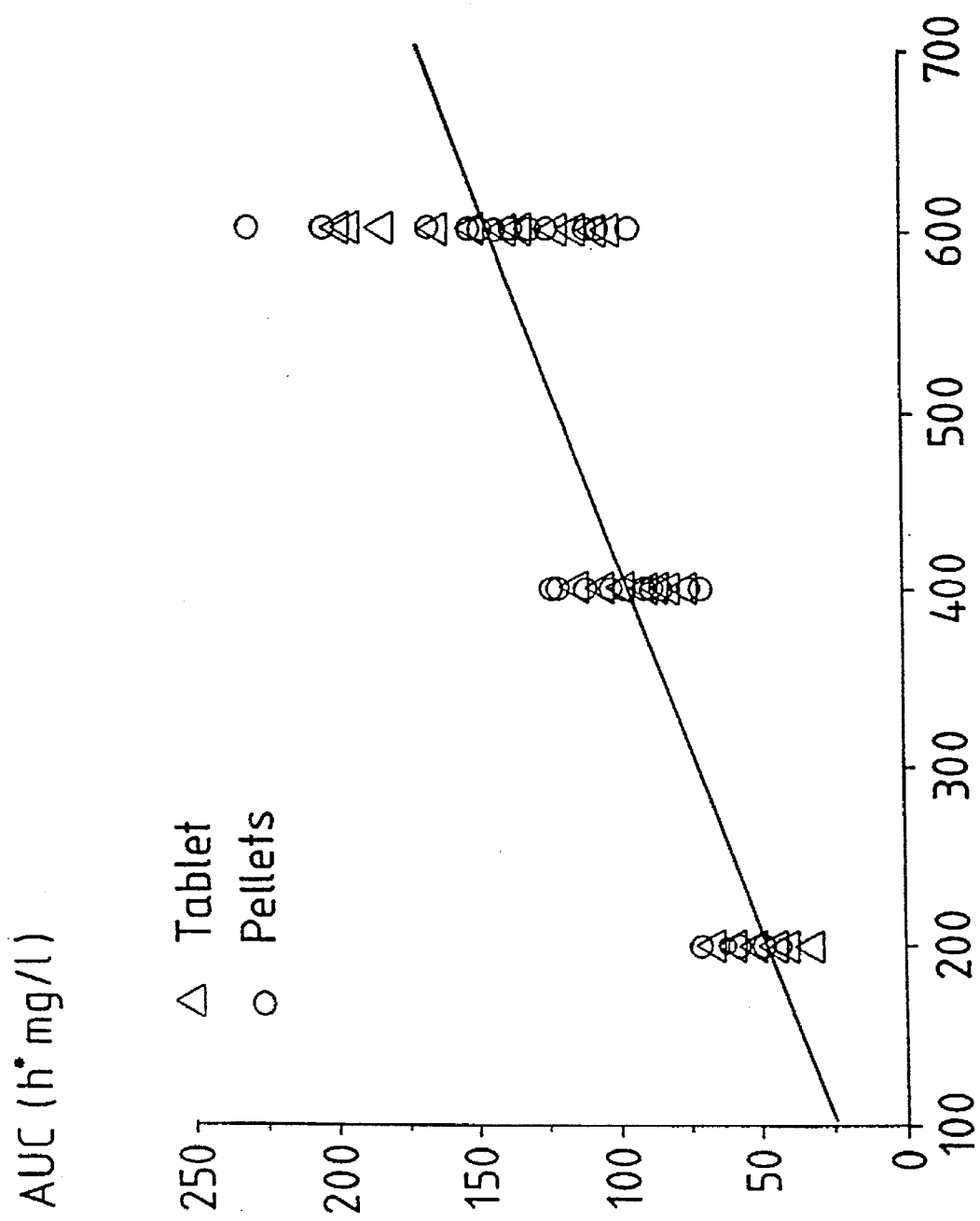
FIG. 15 shows that pellets according to the embodiment of the invention in Example 12 un tablet form and in capsules are bioequivalent in the dose range tested.
Figure 16:
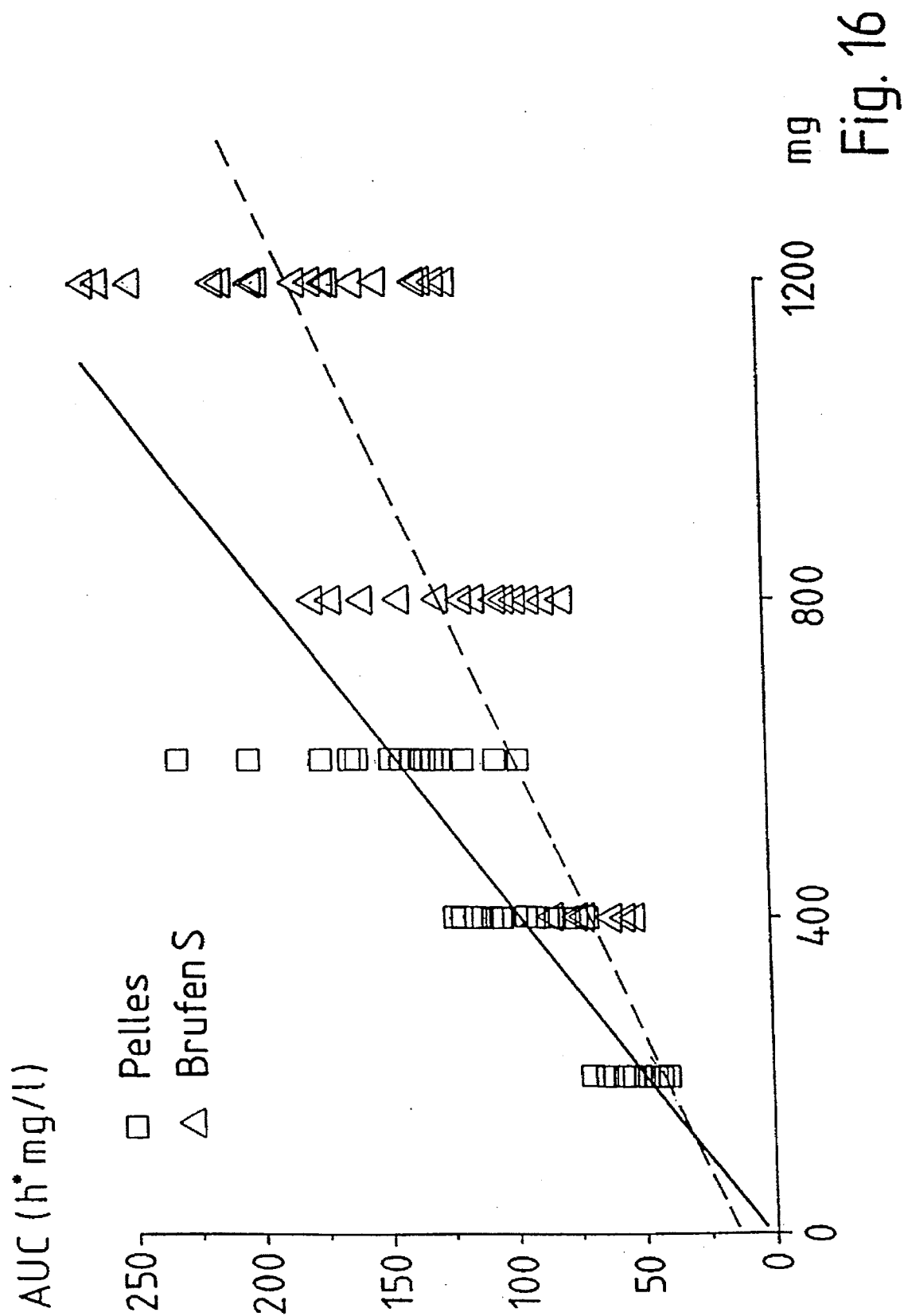
FIG. 16 shows the comparison of S(+)-ubuprofen in the plasma after administration of the pellets of Example 12 in capsules and after administration of Brufen coated tablets, which contain the racemate.
Figure 17:
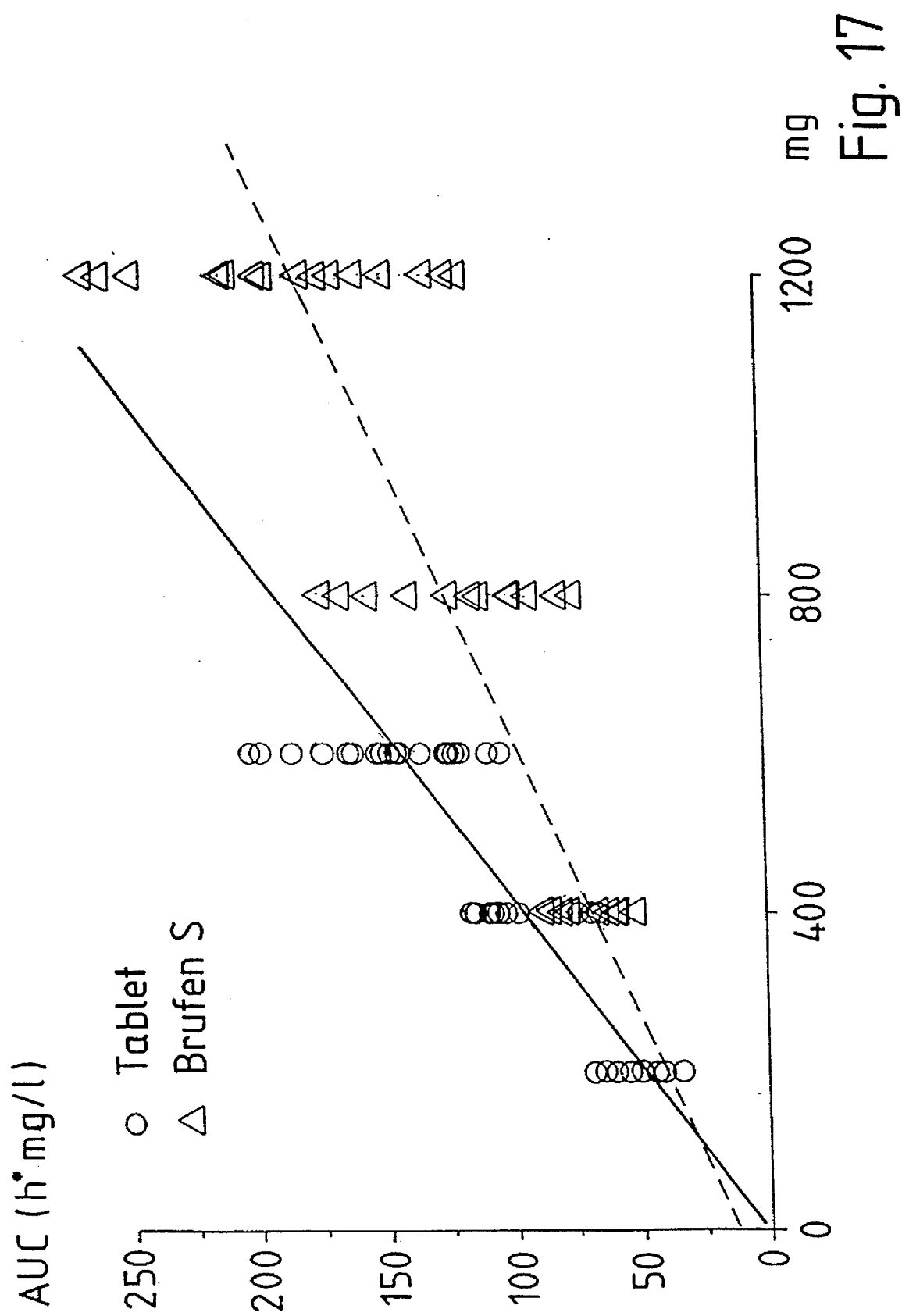
FIG. 17 shows the comparison of S(+)-ibuprofen in the plasma after administration of the pellets of Example 12 in tablets and after administration of Brufen coated tablets, which contain the racemate.

FIG. 12 shows the mean of the ratio of the measured amounts of S(+)-ibuprofen in the subject's plasma (represented as areas under the plasma time/concentration curves=AUC in h*mg/l) to the dose of racemate. FIG. 13 and FIG. 14 show the mean of the ratio for the pellets according to the invention in tablet form and the pellets according to the invention in capsules, respectively. In each case, the amount of S(+)-ibuprofen found in the plasma increases with the dosage administered. FIG. 15 shows that the pellets according to the invention in tablet form and in capsules are bioequivalent in the dose range tested. FIG. 16 compares the S(+)-ibuprofen in the plasma after administration of the pellets according to the invention in capsules and after administration of Brufen coated tablets, which contain the racemate, and FIG. 17 makes the same comparison for pellets according to the invention in tablet form. The following ratios were calculated using regression analysis (means and 95% confidence interval):

tablet according to the invention/coated tablet: 0.68 (0.62–0.73)

capsule according to the invention/coated tablet: 0.67 (0.61–0.73)

Thus, by using pellets according to the invention in tablet form or in capsules, the dosage can be reduced by approx. one third, compared with the racemate, to achieve the same blood levels. This favorable result is obtained by using S(+)-ibuprofen in combination with the pharmaceutical formulations according to the invention, which have a more rapid release characteristic.

What is claimed is:

1. S(+)-Ibuprofen pellets containing 90.0–99.0% by weight of S(+)-ibuprofen and 0.1–10.0% by weight of a basic compound selected from the group consisting of basic inorganic salts, dilute alkali metal hydroxide solutions, and mixtures thereof.

2. Pellets according to claim 1 wherein said basic salt is selected from the group consisting of sodium carbonate, disodium hydrogen phosphate, and potassium carbonate, and said dilute alkali metal hydroxide solution is selected from the group consisting of sodium hydroxide solution and potassium hydroxide solution.

3. Pellets according to claim 1 containing 0.1–5.0% by weight of at least one adjunct.

4. Pellets according to claim 3 wherein said at least one adjunct is selected from the group consisting of microcrystalline cellulose, lactose, HPMC, and silicon dioxide.

5. S(+)-Ibuprofen pellets containing 90.0–99.0% by weight of S(+)-ibuprofen, 0.1–5.0% by weight of silicon dioxide and 0.1–10.0% by weight of sodium carbonate.

6. Coated S(+)-ibuprofen pellets containing 90.0–99.0% by weight of S(+)-ibuprofen and 0.1–10.0% by weight of a basic compound selected from the group consisting of basic inorganic salts, dilute alkali metal hydroxide solutions, and mixtures thereof, said coated pellets having a coating selected from the group consisting of protective coatings, coatings resistant to gastric juice, delayed-release coatings, and mixtures thereof.

7. Coated S(+)-ibuprofen pellets according to claim 6, comprising 0.1–20.0% by weight of a protective coating compound selected from the group consisting of HPMC, HPC, PVP, PVA, MC, methacrylic acids, ethyl acrylates, and mixtures thereof.

8. Coated S(+)-ibuprofen pellets according to claim 6, comprising 0.1–60.0% by weight of a coating compound resistant to gastric juice selected from the group consisting of Eudragit L 30 D, HPMCP, cellulose acetate-phthalate, and mixtures thereof.

9. Coated S(+)-ibuprofen pellets according to claim 6, comprising 0.1–50.0% by weigh of a delayed-release compound selected from the group consisting of Eudragit NE 30 D, Eudragit RS 30 D, Eudragit RL 30 D, ethyl cellulose, and mixtures thereof.

10. Pellets according to claim 6 wherein said protective coating comprises a combination of at least two compounds selected from the group consisting of HPMC, Eudragit L 30 D, talc, titanium dioxide, silicon dioxide, diethyl phthalate, PEG, and antifoam emulsions; said coating resistant to gastric juice comprises a combination of at least two compounds selected from the group consisting of Eudragit L 30 D, diethyl phthalate, silicon dioxide, and antifoam emulsion SE2; and said delayed-release coating comprises a combination of at least two compounds selected from the group consisting of Eudragit RS 30 D, talc, diethyl phthalate, and antifoam emulsion SE2.

11. Pellets according to claim 10 wherein said protective coating comprises HPMC and 0.1–8.0% by weight of talc.

12. Pellets according to claim 10 wherein said protective coating comprises Eudragit L 30 D and further comprises a combination of auxiliary substances containing 0.1–8.0% by weight of each of silicon dioxide and titanium dioxide and 0.1–8.0% by weight of PEG.

13. Pellets according to claim 10 wherein said coating resistant to gastric juice further comprises a combination of auxiliary substances containing 0.1–8.0% by weight of silicon dioxide and 0.1–8.0% by weight of diethyl phthalate.

14. Pellets according to claim 10 wherein said delayed-release coating further comprises a combination of auxiliary substances containing 0.1–8.0% by weight of talc and 0.1–8.0% by weight of diethyl phthalate.

15. Tablets comprising coated S(+)-ibuprofen pellets containing 90.0–99.0% by weight of S(+)-ibuprofen and 0.1–10.0% by weight of a basic compound selected from the group consisting of basic inorganic salts, dilute alkali metal hydroxide solutions, and mixtures thereof,
said coated pellets having a coating selected from the group consisting of protective coatings, coatings resistant to gastric juice, delayed-release coatings, and mixtures thereof,
said coated tablets further comprising 73.0–410.0 mg of at least one tableting auxiliary per 400.0 mg of S(+)-ibuprofen.

16. Tablets comprising coated pellets according to claim 10 and 73.0–410.0 mg of at least one tableting auxiliary per 400.0 mg of S(+)-ibuprofen.

17. Tablets according to claim 15 containing, as tableting auxiliaries, a compound selected from the group consisting of microcrystalline cellulose, calcium hydrogen phosphate, lactose, corn starch, crosscarmellose sodium, sodium starch glycolate, PVP, HPMC, magnesium stearate, hydrogenated castor oil, silicon dioxide, Aerosil 200, potassium chloride, calcium chloride, sodium chloride, sodium citrate, potassium adipate, calcium lactate, potassium citrate, and mixtures thereof.

18. Tablets according to claim 15 comprising 50–800 mg of S(+)-ibuprofen pellets, 15–50% of microcrystalline cellulose, 2.5–20% of corn starch, 0.25–10% of PVP, 0.25–5% of magnesium stearate, 0.25–7.5% of silicon dioxide and 0.025–10% of potassium chloride.

19. A process for the preparation of S(+)-ibuprofen pellets comprising the steps of
mixing S(+)-ibuprofen with at least one adjunct,
spraying the mixture with an aqueous solution in a Diosna mixer or a rotary processor until pellets of the desired size are formed, and
drying said pellets.

20. A process for the preparation of S(+)-ibuprofen pellets according to claim 19, wherein said aqueous solution is a basic solution.

21. A process for the preparation of S(+)-ibuprofen pellets according to claim 19, further comprising the step of fractionating said pellets.

22. A process for the preparation of coated S(+)-ibuprofen pellets comprising the steps of mixing S(+)-ibuprofen with at least one adjunct,
spraying the mixture with an aqueous solution in a Diosna mixer or a rotary processor until pellets of the desired size are formed,
drying said pellets, and
spraying said pellets with a coating.

23. A process for the preparation of S(+)-ibuprofen pellets according to claim 22, wherein said aqueous solution is a basic solution.

24. A method of preparing tablets containing coated S(+)-ibuprofen pellets comprising the step of compressing coated S(+)-ibuprofen pellets directly into tablets with at least one tableting auxiliary.

25. Tablets according to claim 15, wherein the disintegration time under the conditions of USP XXII is less than 2 minutes and the dissolution under the conditions of USP XXII (phosphate buffer, pH 7.2) is over 90% of S(+)-ibuprofen released within 20 minutes.

26. Tablets according to claim 16, wherein the disintegration time under the conditions of USP XXII is less than 2 minutes and the dissolution under the conditions of USP XXII (phosphate buffer, pH 7.2) is over 90% of S(+)-ibuprofen released within 20 minutes.

27. A pharmaceutical composition comprising capsules containing S(+)-ibuprofen pellets according to claim 1 in the dosage range of 50–800 mg, wherein the plasma levels are comparable to those of the racemate on administration of at least 25% less S(+)-ibuprofen than racemate.

28. A method of treating rheumatic, inflammatory, feverish and/or painful diseases in humans and animals, which comprises administering an effective amount of a pharmaceutical composition containing S(+)-ibuprofen pellets according to claim 1.

29. Pellets according to claim 1 containing 96.0–98.0% by weight of S(+)-ibuprofen and 1.0–3.0% by weight of a basic compound selected from the group consisting of basic inorganic salts, dilute alkali metal hydroxide solutions, and mixtures thereof.

30. Pellets according to claim 1 containing approximately 97% by weight of S(+)-ibuprofen and approximately 2.0% by weight of a basic compound selected from the group consisting of basic inorganic salts, dilute alkali metal hydroxide solutions, and mixtures thereof.

31. Pellets according to claim 3 containing approximately 2.0% by weight of at least one adjunct.

32. Pellets according to claim 3 wherein said adjunct is silicon dioxide.

33. Pellets according to claim 5 containing approximately 97% by weight of S(+)-ibuprofen, approximately 1% by weight of silicon dioxide and approximately 2.0% by weight of sodium carbonate.

34. Coated S(+)-ibuprofen pellets according to claim 7, wherein said protective coating compound is approximately 2.0% by weight.

35. Coated S(+)-ibuprofen pellets according to claim 7, wherein said protective coating compound is approximately 10.0% by weight.

36. Coated S(+)-ibuprofen pellets according to claim 7, wherein said protective coating compound is Eudragit L 30 D.

37. Coated S(+)-ibuprofen pellets according to claim 8, wherein said coating resistant to gastric juice is approximately 25.0% by weight.

38. Coated S(+)-ibuprofen pellets according to claim 9 wherein said delayed-release compound is approximately 20.0% by weight.

39. Pellets according to claim 11 wherein said protective coating comprises 2.0% by weight of talc.

40. Pellets according to claim 12 wherein said protective coating comprises 0.4% by weight of each of silicon dioxide and titanium dioxide and 0.2% by weight of PEG.

41. Pellets according to claim 13 wherein said coating resistant to gastric juice comprises 3.0% by weight of silicon dioxide and 1.0% by weight of diethyl phthalate.

42. Pellets according to claim 14 wherein said delayed-release coating comprises a combination of auxiliary substances containing 3.0% by weight of talc and 1.0% by weight of diethyl phthalate.

43. Tablets according to claim 15, containing 240.0–260.0 mg of at least one tableting auxiliary per 400.0 mg of S(+)ibuprofen.

44. Tablets according to claim 15, containing 250.0 mg of at least one tableting auxiliary per 400.0 mg of S(+) ibuprofen.

45. Tablets comprising coated pellets according to claim 10, containing 240.0–260.0 mg of at least one tableting auxiliary per 400.0 mg of S(+)ibuprofen.

46. Tablets comprising coated pellets according to claim 10, containing 250.0 mg of at least one tableting auxiliary per 400.0 mg of S(+)ibuprofen.

47. Tablets according to claim 15 containing 100–400 mg of S(+)-ibuprofen pellets, 40% of microcrystalline cellulose, 10% of corn starch, 3.5% of PVP, 1.5% of magnesium stearate, 3.5% of silicon dioxide and 3.75% of potassium chloride.

* * * * *